US011996198B2

(12) United States Patent
Harte et al.

(10) Patent No.: US 11,996,198 B2
(45) Date of Patent: May 28, 2024

(54) DETERMINATION OF A GROWTH RATE OF AN OBJECT IN 3D DATA SETS USING DEEP LEARNING

(71) Applicant: Aidence IP B.V, Amsterdam (NL)

(72) Inventors: Mark-Jan Harte, Amsterdam (NL); Gerben Van Veenendaal, Amsterdam (NL)

(73) Assignee: AIDENCE IP B.V. (NL)

( * ) Notice: Subject to any disclaimer, the term of this patent is extended or adjusted under 35 U.S.C. 154(b) by 582 days.

(21) Appl. No.: 17/273,230

(22) PCT Filed: Sep. 4, 2019

(86) PCT No.: PCT/NL2019/050574
§ 371 (c)(1),
(2) Date: Mar. 3, 2021

(87) PCT Pub. No.: WO2020/050721
PCT Pub. Date: Mar. 12, 2020

(65) Prior Publication Data
US 2021/0327583 A1 Oct. 21, 2021

(30) Foreign Application Priority Data
Sep. 4, 2018 (NL) ..................................... 2021559

(51) Int. Cl.
*G06T 7/00* (2017.01)
*G16H 30/40* (2018.01)
*G16H 50/20* (2018.01)

(52) U.S. Cl.
CPC ........... *G16H 50/20* (2018.01); *G06T 7/0012* (2013.01); *G16H 30/40* (2018.01);
(Continued)

(58) Field of Classification Search
None
See application file for complete search history.

(56) References Cited

U.S. PATENT DOCUMENTS 8,908,948 B2 * 12/2014 Fan .......................... G06T 7/143
382/128
10,074,039 B2 * 9/2018 Mitsumoto ............. G06F 18/24
(Continued)

FOREIGN PATENT DOCUMENTS

CN 106056595 A 10/2016
CN 107636659 A 1/2018
(Continued)

OTHER PUBLICATIONS

International Search Report and Written Opinion for corresponding International application No. PCT/NL2019/050574; dated Dec. 10, 2019 (20 pages).
(Continued)

*Primary Examiner* — Vikkram Bali
(74) *Attorney, Agent, or Firm* — Mendelsohn Dunleavy, P.C.

(57) ABSTRACT

A method for automated determination of a growth rate of an object in 3D data sets is described wherein the method may comprise: a first trained 3D detection deep neural network (DNN) determining one or more first VOIs in a current 3D data set and second VOIs in prior 3D data set, a VOI being associated with an abnormality; a registration algorithm, preferably a registration algorithm based on a trained 3D registration DNN, determining a mapping between the one or more first and second VOIs, the mapping providing for a first VOI in the current 3D data set a corresponding second VOI in the prior 3D data set; a second trained 3D segmentation DNN segmenting voxels of a first VOI into first voxels representing the abnormality and voxels of a corresponding second VOI into second voxels representing the abnormality; and, determining a first volume of the abnormality on the basis of the first voxels and a second volume of the abnor-
(Continued)

mality on the basis of the second voxels and using the first and second volume to determine a growth rate.

21 Claims, 15 Drawing Sheets

(52) U.S. Cl.
CPC .............. *G06T 2207/10081* (2013.01); *G06T 2207/20081* (2013.01); *G06T 2207/20084* (2013.01)

(56) References Cited

U.S. PATENT DOCUMENTS

| | | | |
|---|---|---|---|
| 10,169,685 B2* | 1/2019 | Chen | G06T 7/187 |
| 2011/0216951 A1 | 9/2011 | Ye et al. | |
| 2013/0083023 A1* | 4/2013 | Fram | G06T 19/00 345/424 |
| 2014/0016845 A1 | 1/2014 | Gazit et al. | |
| 2015/0279034 A1 | 10/2015 | Knapp et al. | |
| 2016/0005193 A1 | 1/2016 | Markov et al. | |
| 2017/0024884 A1 | 1/2017 | Ishihara et al. | |
| 2018/0089530 A1 | 3/2018 | Liu et al. | |
| 2018/0116620 A1 | 5/2018 | Chen et al. | |
| 2018/0143275 A1 | 5/2018 | Sofka et al. | |

FOREIGN PATENT DOCUMENTS

| | | |
|---|---|---|
| CN | 107997778 A | 5/2018 |
| JP | 2008-173213 A | 7/2008 |
| JP | 2011-177517 A | 9/2011 |
| JP | 2017-23551 A | 2/2017 |
| WO | 2018026431 A1 | 2/2018 |
| WO | 2019030410 A1 | 2/2019 |

OTHER PUBLICATIONS

International Preliminary Report on Patentability for corresponding International application No. PCT/NL2019/050574; dated Nov. 18, 2020 (27 pages).
Christ, Patrick Ferdinand, et al. "Automatic Liver and Tumor Segmentation of CT and MRI Volumes Using Cascaded Fully Convolutional Neural Networks." Retrieved from Internet <URL:https://arxiv.org/pdf/1702.05970.pdf> (2017): 1-20.
Wang, Guotai, et al. "Automatic Brain Tumor Segmentation Using Cascaded Anisotropic Convolutional Neural Networks." BrainLes 2017, Lecture Notes in Computer Science, vol. 10670, Springer (2018): 178-190.
Wiemker, Rafael, et al. "Aspects of computer-aided detection (CAD) and volumetry of pulmonary nodules using multislice CT." The British Journal of Radiology, vol. 78 (2005): S46-S56.
Yamashita, Rikiya, et al. "Convolutional neural networks: an overview and application in radiology", Insights Into Imaging vol. 9.4 (2018): 611-629.
Zhao, Yiyuan, et al. "A deep-learning based automatic pulmonary nodule detection system." Progress In Biomedical Optics and Imaging, SPIE—International Society for Optical Engineering, vol. 10575 (2018): pp. 1057537-1 to 1057537-7.
First Office Action for corresponding Chinese application No. 201980073082.3; dated Apr. 13, 2023 (20 pages) Machine Translation.
Notice of Reasons for Rejection for corresponding Japanese application No. 2021-513260; dated Apr. 24, 2023 (8 pages).

* cited by examiner

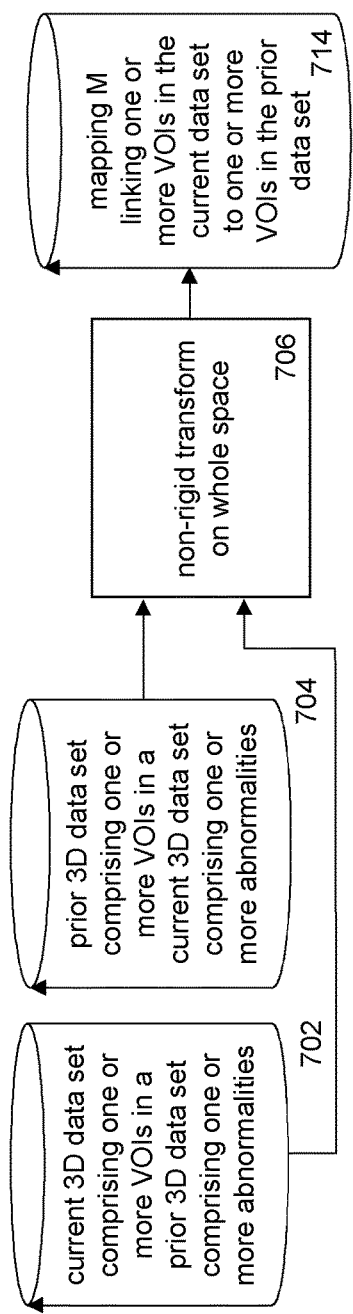
FIG. 7
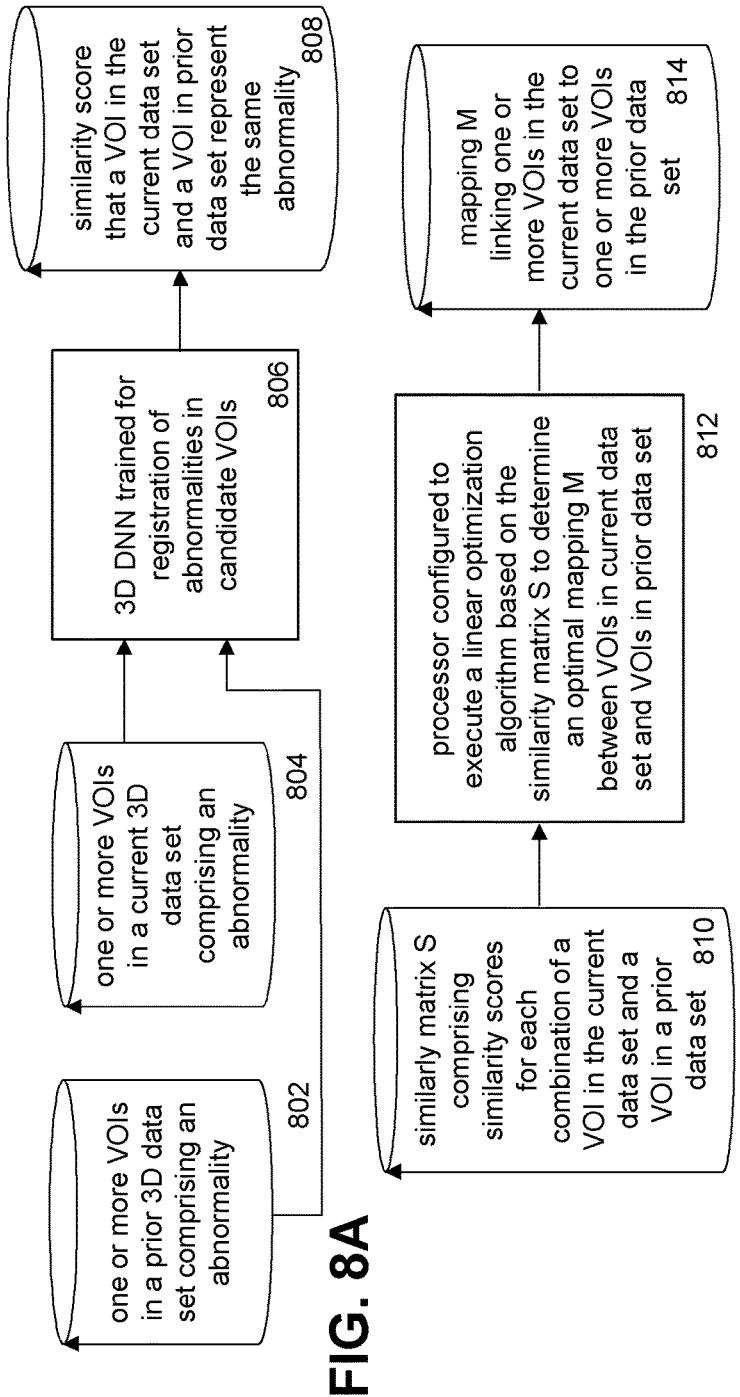
FIG. 8A
FIG. 8B

DETERMINATION OF A GROWTH RATE OF AN OBJECT IN 3D DATA SETS USING DEEP LEARNING

FIELD OF THE INVENTION

The invention relates to automatic determination of a growth rate of an object in 3D data sets using deep learning; and, in particular, though not exclusively, to methods and systems for automated determination of a growth rate of an object in 3D data sets using deep learning, training methods for training deep neural networks for automated determination of a growth rate of an object in 3D data sets and a computer program product executing such a method.

BACKGROUND OF THE INVENTION

Abnormalities or lesions are the precursor to cancer. Early detection of these lesions is therefore an important radiological task that allows for curative intervention. The cost-effectiveness of screening for lung nodules was proven by the National Lung Screening Trial (NLST) of the US National Cancer Institute. Hence, computer-aided detection and diagnostic (CAD) systems have been developed that can help in setting up an efficient and reliable screening scheme. Such CAD systems have been on the market for a number of years now and enable (semi)-automated detection of lung nodules. Typically, these systems suffer from a low sensitivity (or conversely very high false-positive rate) and therefore achieved low adoption by the medical profession. With the recent advances in deep learning techniques, lung nodule detection has become more accurate and AI-based systems are in development by several companies. A highly accurate detection model for detecting abnormalities in 3D data sets, e.g. 3D x-ray data generated by scanning systems such as an CT scanning system, has been successfully developed by the applicant and is cleared for regulatory use.

Information that a medical specialist can derive from a 3D data set include size, volume and shape of an abnormality. Additionally, based on a time series of 3D data sets a growth rate of an abnormality can be derived. Such parameters can be of great diagnostic importance. Automatic determination of such parameters however is not a trivial task for a computer. While it is theoretically possible to manually detect and segment an abnormality in each image it appears, in practice such approach is very time-consuming and prone to errors or at least inaccuracies. Therefore, traditionally computer-aided detection and diagnostic system use computer vision and machine learning algorithms to create a segmentation of an abnormality by having a qualified user manually selecting a 'seed point' and applying well-known 'region growing' algorithms to find the boundaries of such abnormality semi-automatically. For example, R. Wiemker et. al, describe in their article Aspects of computer-aided detection (CAD) and volumetry of pulmonary nodules using multislice CT, The British Journal of Radiology, 78 (2005), a system for detection, segmentation and registration of nodules. The detection, segmentation and registration are separate tasks performed by a human operator, and does not provide a single automated pipeline. Furthermore, the segmentation is based on a region growing method and the registration is based on a rigid affine transform. Such scheme has a significant drawback of requiring a user to switch his radiological workflow away from his reading flow and perform a manual action in a different software application. This takes several minutes and is often not done in practice. Instead, a 2D measurement using digital calipers is performed as an approximation out of necessity so that the information derived by the radiologist from the images is not very accurate. More generally, know CAD systems for detection and volumetric quantification of nodules in CT scans that rely on conventional image processing techniques do not provide a fully automated system providing volumetric information about nodules with an accuracy that at least matches the accuracy of a medical expert.

Recently deep learning techniques are successfully used for automatic detection of pulmonary nodules. Zhao et al, described in their article "A deep-learning based automatic pulmonary nodule detection system", SPIE, Medical Imaging 2018: Computer-Aided Diagnosis, 27 Feb. 2018, a system for detecting nodules in CT images comprising two deep neural networks. This article illustrates that deep neural networks are useful for analyzing complex 3D data sets such as 3D CT scans. These systems however only deal with detection and localization of abnormalities in CT scans. These systems do not deal with automatic and accurate determination of a growth rate of an abnormality in 3D data sets such as CT scans based on deep learning, i.e. a system that derives parameters about detected abnormalities without any human intervention and with an accuracy that is at least as similar to that of a medical expert. Hence, from the above it follows that here is a need in the art for improved methods and systems for automated registration of an object, e.g. an abnormality, in 3D data sets and automated determination of a growth rate of a registered object in the 3D data using deep learning.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can comprise, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including a functional or an object oriented programming language such as Java™, Scala, C++, Python or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer, server or virtualized server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or central processing unit (CPU), or graphics processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

In an aspect, the invention relates to a method for automated determination of a growth rate of an object in 3D data sets. In an embodiment, the method may comprise: a first trained 3D detection DNN determining one or more first VOIs in a current 3D data set and second VOIs in prior 3D data set, a VOI being associated with an abnormality; a registration algorithm, preferably a registration algorithm based on a trained 3D registration DNN, determining a mapping between the one or more first and second VOIs, the mapping providing for a first VOI in the current 3D data set a corresponding second VOI in the prior 3D data set; a second trained 3D segmentation DNN segmenting voxels of a first VOI into first voxels representing the abnormality and voxels of a corresponding second VOI into second voxels representing the abnormality; and, determining a first volume of the abnormality on the basis of the first voxels and a second volume of the abnormality on the basis of the second voxels and using the first and second volume to determine a growth rate.

In a further embodiment, the method may comprise a processor providing a current 3D data set associated with a first time instance to the input of a first 3D deep neural network (DNN) system, the current 3D data set defining voxel representations of a body part of a patient, the first 3D DNN system being trained to receive a 3D data set and, if the 3D data set comprises one or more abnormalities (e.g. a nodule or a lesion), to output one or more VOIs in the 3D data set respectively; and in response to the input the processor receiving one or more first VOIs in the current 3D data set from the output of the first 3D DNN; the processor providing a prior 3D data set associated with a second time instance to the input of the first 3D deep neural network (DNN) system, the prior 3D data set defining voxel representations of the body part of the patient; and, in response to the input the processor receiving one or more second VOIs in the prior 3D data set from the output of the first 3D DNN; the processor using a registration algorithm to register the one or more first VOIs with the one or more second VOIs, the registration algorithm generating a mapping, the mapping determining for a first VOI in the current 3D data set a corresponding second VOI in the prior 3D data set, the processor using the mapping to determine that the first and second VOI comprising voxels relating to the same abnormality; the processor providing voxels of the first VOI and the corresponding second VOI to the input of a second 3D DNN, the second 3D DNN being trained to receive voxels of a VOI and to output a 3D map defining probabilities for voxels of the VOI, a probability associated with a voxel defining a chance that the voxel is part of an abnormality, the processor receiving a first 3D map and a second 3D map from the output of the second 3D DNN and using the first 3D map to identify first voxels in the current 3D data set representing the abnormality and the second 3D map to identify second voxels in the prior data set representing the abnormality; and, the processor determining a first volume of the abnormality based on the first voxels and a second volume of the abnormality based on the second voxels and using the first volume and second volume to determine a growth rate. Hence, the invention provides a fully automated process for accurately determining the growth rate of abnormalities, e.g. nodules or lesions, in 3D data sets, e.g. 3D CT scans generated by a scanning device. The use of trained deep neural networks provides a system that can determine the growth rate and the volume of abnormalities at least as accurate as a medical expert. Valuable information for accurate and fast interpretation of CT scans can be provided automatically and on the fly.

In an embodiment, the method may further comprise: after the processor receiving the one or more first VOIs, the processor using metadata associated with the current 3D data set to construct a request message and to send the request message to a database, preferably a picture archiving and communication system (PACS), the request message instructing the database to send a prior 3D data set of the same patient and the same body part to the processor. Thus, the prior 3D data set will be automatically retrieved based on metadata of the current 3D data set.

In an embodiment, the first trained 3D deep neural network system may include at least a first 3D deep convolutional neural network (CNN), preferably a deep fully convolutional neural network, trained to receive a 3D data set at its input and to determine locations within the 3D data set of one more one candidate VOIs at its output, each candidate VOI defining a location in the 3D data set at which an abnormality may be present; and, at least a second 3D deep CNN, trained to receive a candidate VOI from the output of the first 3D CNN and to determine a probability regarding the chance that voxels of a candidate VOI represent an abnormality. Hence, the deep neural network system for detecting abnormalities includes a first 3D CNN for generating candidates VOIs and a second 3D CNN evaluating the candidate VOIs for reducing false positives.

In an embodiment, the registration algorithm may include a non-rigid transform to register voxels of the current 3D data set with voxels of the prior 3D data set.

In an embodiment, the registration algorithm may comprise a third 3D deep neural network (DNN) system trained to receive a first VOI of the current 3D data set and a second VOI of the prior 3D data at its input and to determine a similarity score at its output, the similarly score defining a measure regarding the similarity between voxels of the first VOI and voxels of the second VOI. In contrast with existing registration algorithms which register all voxels of both 3D data sets, the registration based on a trained DNN registers the VOIs in the 3D data sets. This process is therefore considerably less computational intensive.

In an embodiment, the third 3D DNN may be configured as a 3D deep siamese neural network, the siamese neural network including a first 3D deep neural network part, preferably a first 3D deep CNN, for receiving and processing the first VOI and a second 3D deep neural network part, preferably a second 3D deep CNN, wherein the first and second 3D deep neural network parts share the same weights.

In an embodiment, the registration algorithm generating a mapping may include: determining a similarity matrix comprising probability scores associated with combinations of a first VOI selected from the one or more first VOIs in the current 3D data set and a second VOI selected from the one or more second VOIs in the prior 3D data set; using a linear optimization algorithm based on the similarity matrix to determine an optimal mapping between the one or more first VOIs of the current 3D data set and the one or more second VOIs of the prior 3D data set.

In an embodiment, a first threshold may be applied to the probabilities in first 3D map to form a first binary 3D map identifying the first voxels in the current 3D data set and a second threshold is applied to the probabilities in the second 3D map to form a second 3D binary map to identify the second voxels in the prior 3D data set respectively.

In an embodiment, the first threshold may be selected such that the sum of voxel volumes identified by the first 3D binary map represents the volume of the abnormality in the current 3D data set and the second threshold may be selected such that the sum of voxel volumes identified by the second 3D binary map represents the volume of the abnormality in the prior 3D data set. Hence, in this embodiment, the probabilistic 3D map generated by the 3D DNN on the basis of a VOI (wherein the sum of the probabilities of the map represent a measure of the volume V of the abnormality) is transformed to a binary 3D map, wherein the sum of the voxels identified by the binary 3D map represents an estimate of the volume of the abnormality.

In an embodiment, the method may further comprise: generating a digital report associated with the current 3D data set and the prior 3D data set, the digital report including a 3D graphical representation of the abnormality in the current 3D data set and a 3D graphical representation of the abnormality in the prior 3D data set and the growth rate of the abnormality.

In an embodiment, the first 3D DNN system and/or the second DNN may comprise one or more blocks of convolutional layers, each block including a 3D CNN and a 2D CNN, wherein a reshaping operation reshape slices of the 3D CNN into a plurality of 2D slices, wherein each slice is processed by the 2D CNN.

In an embodiment, the 2D CNN may be configured as a 2D residual CNN.

In an embodiment, the first 3D DNN system or the third 3D deep neural network may comprise a 3D residual convolutional neural network.

In an embodiment, the storage and the retrieval of the current and prior 3D data set may be based on the DICOM standard.

In a further aspect, the invention may relate to a method of training a plurality of 3D deep neural networks including: a processor receiving a training set for training a plurality of 3D DDNs, the training set including 3D data sets, preferably 3D CT scans, of a body part of a patent, wherein each of the 3D data sets either comprise zero or one or more abnormalities (e.g. lesions or nodules); one or more volume of interests (VOIs) for at least part of the 3D data sets, each VOI being associated with an abnormally; receiving for each VOI: a pixel representations of the VOI, location information indicating at which location the VOI is located in a 3D data set and a probabilistic 3D map defining probabilities for voxels of the VOI, a probability associated with a voxel defining a chance that the voxel is part of an abnormality;

training a first 3D deep neural network using voxel representations of the 3D data sets as input and the location information as target; training a second 3D deep neural network using voxel representations of the VOIs as input and probabilistic 3D maps associated with the voxel representations of the VOIs as target; and, training a third 3D deep neural network using voxel representations of the VOIs and non-linear image transformations of the voxel representations of the VOIs as input and similarity scores as target, a similarity score defining a similarity between a voxel representation of a VOI and a non-linear image transformations of the voxel representation.

In an aspect, the invention may relate to a computer system for automated determination of a growth rate of an object in 3D data sets, comprising: a computer readable storage medium having computer readable program code embodied therewith, the program code including at least one trained 3D deep neural network, and at least one processor, preferably a microprocessor, coupled to the computer readable storage medium, wherein responsive to executing the computer readable program code, the at least one processor is configured to perform executable operations comprising: providing a current 3D data set associated with a first time instance to the input of a first 3D deep neural network (DNN) system, the current 3D data set defining voxel representations of a body part of a patient, the first 3D DNN system being trained to receive a 3D data set and, if the 3D data set comprises one or more abnormalities (e.g. a nodule or a lesion), to output one or more VOIs in the 3D data set respectively; and in response to the input the processor receiving one or more first VOIs in the current 3D data set from the output of the first 3D DNN; providing a prior 3D data set associated with a second time instance to the input of the first 3D deep neural network (DNN) system, the prior 3D data set defining voxel representations of the body part of the patient; and, in response to the input the processor receiving one or more second VOIs in the prior 3D data set from the output of the first 3D DNN; using a registration algorithm to register the one or more first VOIs with the one or more second VOIs, the registration algorithm generating a mapping, the mapping determining for a first VOI in the current 3D data set a corresponding second VOI in the prior 3D data set, the processor using the mapping to determine that the first and second VOI comprising voxels relating to the same abnormality; providing voxels of the first VOI and the corresponding second VOI to the input of a second 3D DNN, the second 3D DNN being trained to receive voxels of a VOI and to output a 3D map defining probabilities for voxels of the VOI, a probability associated with a voxel defining a chance that the voxel is part of an abnormality, the processor receiving a first 3D map and a second 3D map from the output of the second 3D DNN and using the first 3D map to identify first voxels in the current 3D data set representing the abnormality and the second 3D map to identify second voxels in the prior data set representing the abnormality; and, determining a first volume of the abnormality based on the first voxels and a second volume of the abnormality based on the second voxels and using the first volume and second volume to determine a growth rate.

In an embodiment, the computer system for automated determination of a growth rate of an object in 3D data sets may implement any of the method steps as described above.

The invention may also relate to computer program product comprising software code portions configured for, when run in the memory of a computer, executing the method steps according to any of the claims as described above.

In a further aspect, the invention may also relate to a computer program product comprising software code portions configured for, when run in the memory of a computer, executing the method steps according to any of the process steps described above.

The invention will be further illustrated with reference to the attached drawings, which schematically will show embodiments according to the invention. It will be understood that the invention is not in any way restricted to these specific embodiments.

BRIEF DESCRIPTION OF THE DRAWINGS

FIG. 7 depicts a registration module according to an embodiment of the invention;

FIG. 8 depicts a registration module according to another embodiment of the invention;

DETAILED DESCRIPTION

Figure 1:
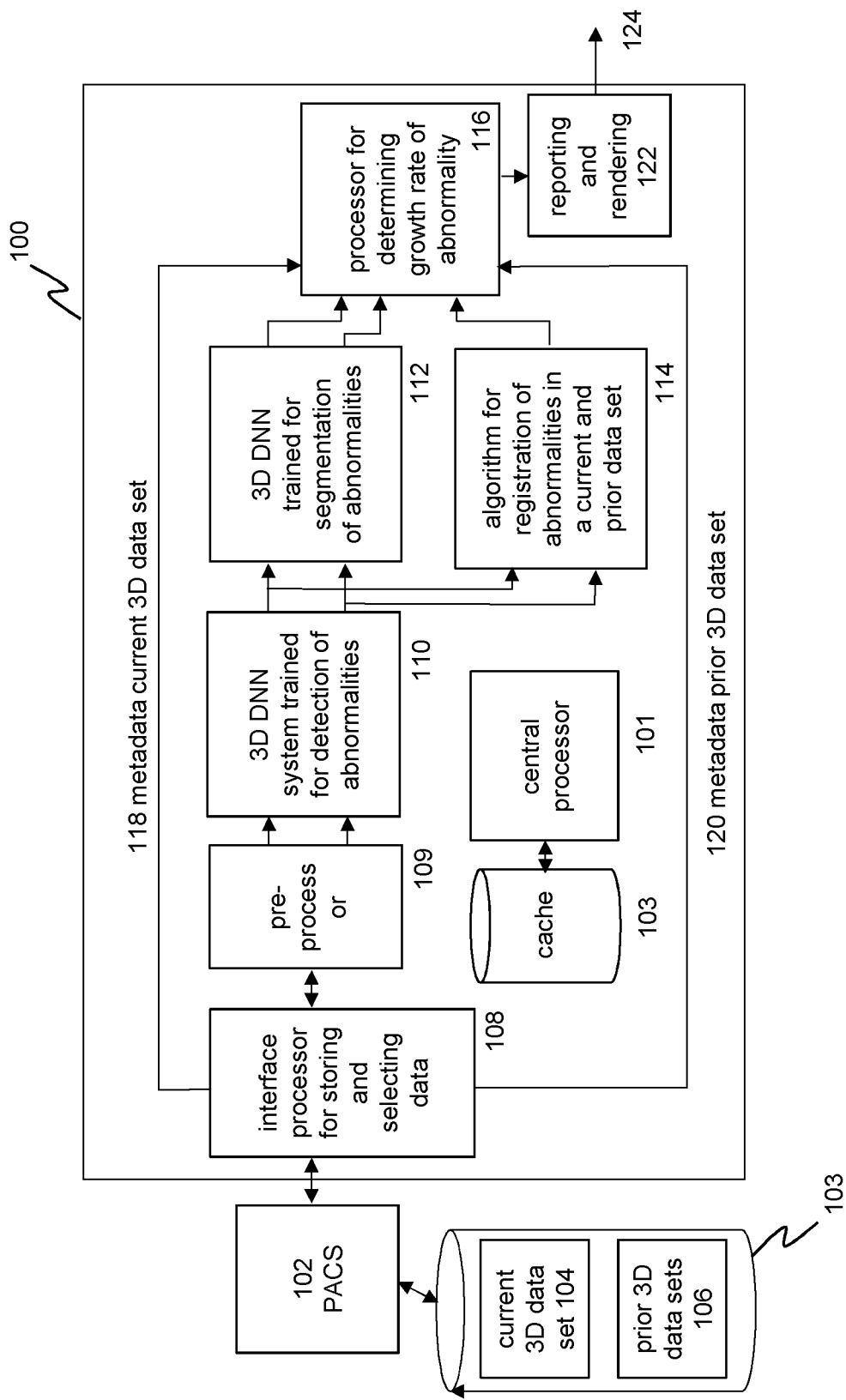
FIG. 1 depicts a system for automatic determining a growth rate of an abnormality in 3D data sets according to an embodiment of the invention.

In this disclosure embodiments are described of computer systems and computer-implemented methods that use 3D deep neural networks (DNNs) for automated determination of one or more objects, e.g. on or more tissue abnormalities such as lesions or nodules, in 3D data sets generated by a scanning system, e.g. an X-ray scanning system such as a CT scanning system or a CBCT scanning system. Generally, such scanning systems are configured to generate 3D data sets wherein each 3D data set defines a 3D representation of a body part of a patient. The systems may include a module configured for automatic detection of tissue abnormalities in 3D data sets based on deep learning. Further, the systems may include a module configured for segmentation of detected tissue abnormalities in 3D data sets based on deep learning. Additionally, the systems may include a module for registration of detected tissue abnormalities in different 3D data sets of the same patient, e.g. a current 3D data set and a current 3D data set, based on deep learning. Finally, the systems may include a module for determining a growth rate of a registered tissue abnormality. The module may be based on deep learning or another algorithm. A processor of the system may control the modules so that a growth rate of a tissue abnormality that is detected in a current 3D data set can be fully automatically determined without any human intervention. The growth rates determined by the system may have an accuracy that is at least comparable to a golden standard (a ground truth) which is based on a medical specialist interpreting and processing the 3D data using e.g. a software application. Exemplary embodiments of the invention are described hereunder in more detail FIG. 1 depicts a system according to an embodiment of the invention. In particular, FIG. 1 depicts a system 100 for automated determination of a growth rate of an object in 3D data sets. The system may be implemented on one or more computers that are configured to execute a plurality of modules, including 3D deep neural networks that may be trained to receive (part(s) of) one or more 3D data sets as their input and process the data according to a training model. The system may be implemented as a stand-alone system (e.g. a server system or a network application such as a cloud application) connected to data storage and retrieval system 102, e.g. a database system or the like, including one or more storage units 103, e.g. databases, of the PACS system. The 3D data sets may include a current 3D data set 104, i.e. a 3D data set of a patient that is to be processed by the system and one or more prior 3D data sets 106, i.e. earlier 3D data sets of the same patient. In the medical field, such data storage and retrieval system may be referred to as a picture archiving and communication system (PACS). Alternatively, at least part of the system may be part of a scanning system, e.g. a CT scanning system or the like.

The PACS system may be connected via a network connection, e.g. the Internet, to other computers (not shown), e.g. one or more servers of scanning system located at different hospitals. A 3D data set may define a 3D representation of a body part of a patient wherein the data may be arranged according to a certain data format. For example, in an embodiment, the 3D data set may define a voxel representation of X-ray data generated by a (CB)CT scanner. Each voxel may define a unit volume of certain dimensions in a 3D grid, wherein each voxel may be associated with a voxel value, e.g. a radio density, measured in Hounsfield Units (HUs). The 3D data sets may be stored as a file of a certain format, e.g. the DICOM format. A 3D data set may be regarded as a series of 2D data sets where each 2D data set has a different acquisition plane (of e.g. a sagittal or coronal type). Typically, the voxels of a 3D data set are anisotropic in terms of resolution, i.e. the resolution in the xy direction is substantially higher than the resolution in the z-direction.

Further, a 3D data set may include metadata including information about the type of acquisition plane, the reconstruction kernel that was used by the image processing computer of the scanning system that generated the 3D data set and time information, e.g. a timestamp, defining the time that the data were generated by the scanning system. Here, the reconstruction kernel may be associated with a filtered-forward projection algorithm that was used to generate a voxel representation from the detector outputs of the scanning system. The metadata may have a DICOM format.

The system may include an interface processor 108 for interfacing with external systems, including the PACS, system. As will be described hereunder in greater detail, the processor may include an application, e.g. a client application, configured to communicate with the PACS system using for example a client-server protocol for accessing the database. Communication with the PACS system may be based on a known protocol. For example, e.g. a DICOM Query/Retrieve protocol may be used to access 3D data sets that have a DICOM format. The interface processor may be further configured to process metadata associated with files comprising 3D data sets that are processed by the system and to provide modules in the system with relevant metadata. The interface processor is further connected to a data processing pipeline of modules comprising trained 3D deep neural networks. A pre-processing module 109 may be configured to pre-process a 3D data set before the data set is offered to the input one of the modules of the data processing pipeline. The pre-processing may include a normalization process which takes care that the 3D data sets (current and prior) that are going to be processed by the further modules in the data processing pipeline all have the same resolution in all 3D dimension.

The system is configured to automatically determine a growth rate of a tissue abnormality, e.g. lesion, (e.g. as a 'volume doubling time' or 'VDT'). To that end, the system, e.g. the central processor may determine that the interface processor receives a current 3D data set of a patient (generated at time instance $T_1$) from the PACS system and forward the received current 3D data set to the detection module for determining one or more VOIs in the current 3D data set comprising wherein each VOI includes voxels associated with an abnormality. If such VOI is detected, the central processor may instruct the interface processor to look for a relevant prior 3D data set (generated at an earlier time instance $T_0$) of the same patient. Further, if the central processor determines that the interface processor has determined a relevant prior 3D data set, it may forward the prior 3D data set to the detection module to determine one or more VOIs in the prior 3D data set. If one or more VOIs are detected in both the current and prior 3D data set, the central processor may instruct the registration module to evaluate the detected VOIs in the current and prior 3D data sets in order to determine whether voxels of a VOI in the current data set and voxels of a VOI in the prior data represent the same abnormality. Further, the central processor may instruct the segmentation module to classify voxels in a detected VOI as being part of an abnormality detected. The volume of voxels that are classified as voxels belonging to an abnormality can be used to derive a volume of the abnormality. Preferably, segmentation of the current and prior 3D data set is performed based on the same version of the segmentation algorithm, as it is known that variations in the algorithm may cause variances in the volume that can be derived from segmented voxels.

Further, based on the metadata associated with the processed 3D data sets an elapsed time between the scans can be determined. The volumes of the abnormalities and the elapsed time can be used to determine a measure for the growth rate of the abnormality. For example, a growth rate parameter for diagnoses and/or treatment is the so-called "volume doubling time", which is defined by the following formula:

$$VDT = \frac{\ln 2 \cdot (T_1 - T_0)}{\ln\left(\frac{V_1}{V_0}\right)}$$

where $V_0$ and $V_1$ are volumes of the tissue abnormality at time instances $T_0$ and $T_1$ respectively. If $V_0 = V_1$ or if the difference between $V_0$ and $V_1$ is very small the numeric value of the VDT becomes numerical unstable. In that case, another metric such as e.g. the growth percentage (GP) may be calculated by the system:

$$GP = \frac{V_1 - V_0}{V_0} \times 100\%$$

As the system automatically determines a growth rate based on a current 3D data set, system may be automatically retrieve a relevant prior 3D data set. To that end, the interface processor may generate protocol messages for accessing the database and retrieve a 3D data set based on query criteria and evaluation of the metadata, e.g. the DICOM metadata tags, of the current 3D data set. The system is configured to determine the growth rate with an accuracy that is at least as accurate as the determination of a growth rate on the basis of 3D data sets by a medical specialist.

In order to realize a system that is capable of automatically determining an accurate measure of the growth rate of an abnormality, the system may include a detection module 110 including a 3D deep neural network system trained for detecting abnormalities in a 3D data set, a segmentation module 112 including a 3D deep neural network trained for segmenting an abnormality detected by the detection module and a registration module 114 configured to register an abnormality based on an abnormality detected in a current and a prior 3D data set. The output of the segmentation module (segmented voxels of a detected abnormality in a current and prior 3D data set) and the output of the registration module (measure regarding the similarity of detected abnormality in the current and prior 3D data set) may be fed to the input of a growth rate module 116. The growth rate module may be further configured to receive metadata of 3D data sets that are processed by the module (e.g. metadata 118 of the current 3D data set and metadata 120 of the prior 3D data set) which is needed in order to determine a measure for the growth rate 122. The retrieval of 3D data sets and the processing of 3D data sets by the modules in the system may be controlled by a central processor 101.

Hence, in contrast with the prior art wherein a specialist estimates a growth rate based on information provided by an image processing system, the invention provides a system that automatically determines a growth rate of an abnormality in a 3D data set that is provided to the input of the system. The accuracy of the growth rate is at least as accurate as a golden standard in which a medical specialist processes the 3D data sets by manual examination and segmentation of 2D slices of and by determining a volume based on the thus segmented 3D data. The accuracy is provided by a set of deep neural networks that are specifically designed and trained for specific functions within the data processing pipeline of the system. The modules, the deep neural networks and the processes executed by the modules are described hereunder in more detail.

Figure 2:
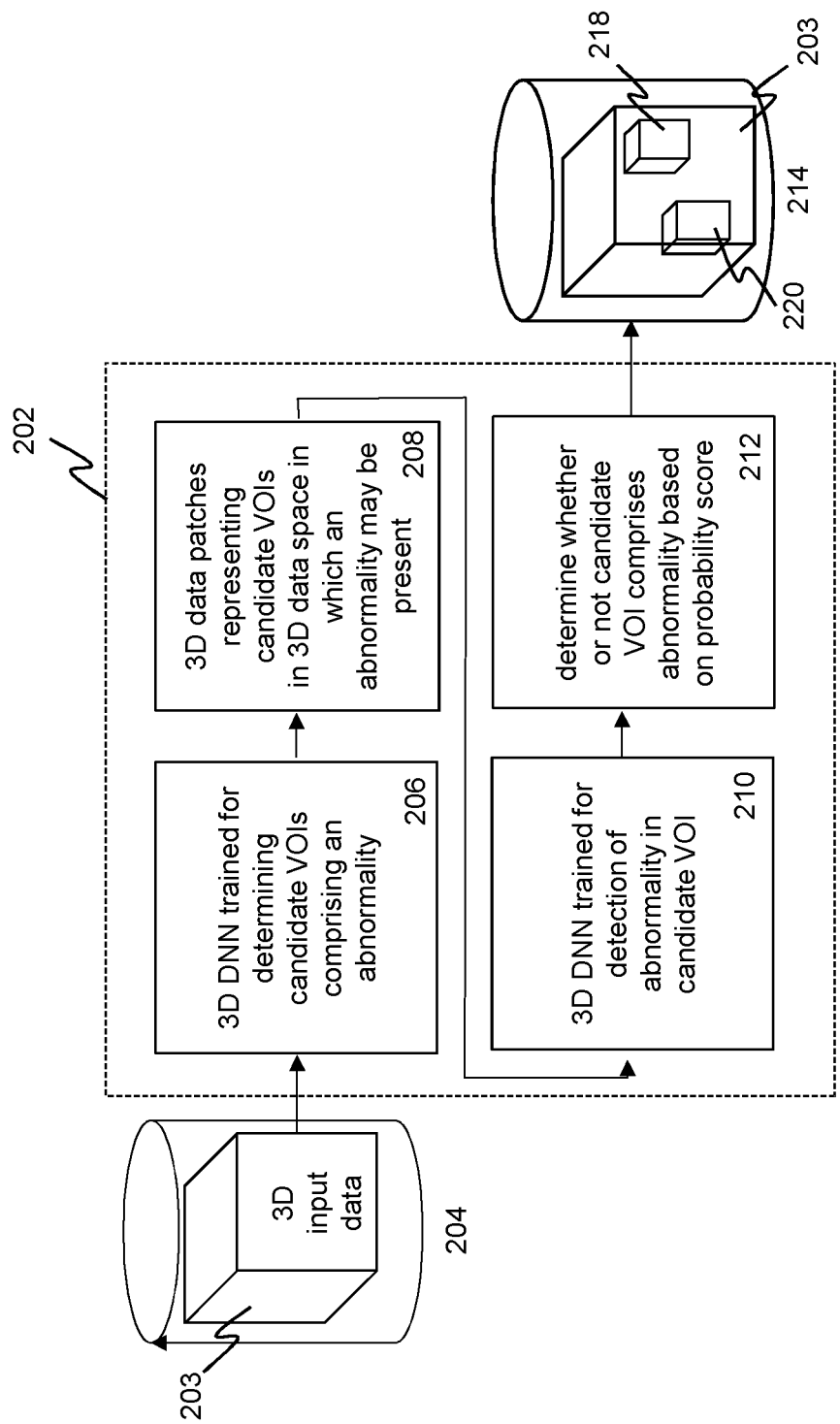
FIG. 2 depicts a detection module based on a 3D deep neural network system according to an embodiment of the invention.

FIG. 2 depicts a detection module based on a 3D deep neural network system according to an embodiment of the invention. As shown in this figure, the detection module 202 may comprise (at least) two 3D deep neural networks, a first 3D deep neural network and a second 3D deep neural network 210. The first 3D deep neural network 206 may be trained to determine one or more positions of volume of interests (VOIs) within a space, e.g. a voxel space, of a 3D data set 204 that wherein each VOI may comprise an abnormality. Input data in the form of a set of voxels 203 (e.g. a 3D data set or at least a substantial part of it may be offered to the input of the trained first deep neural network and in response the first 3D deep neural network may identify positions of candidate VOIs that may include an abnormality. A set of voxels around a position of a candidate VOI may be evaluated by the 3D second deep neural network, which is trained to receive at its input a set of voxels of a candidate VOI in a 3D data set and to generate a probability regarding whether the VOI comprises an abnormality or not. A threshold value may be used to determine whether the probability determined by the network is high enough for the detection module to conclude that the VOI comprises voxels representing an abnormality. This way, output data 214 of the detection module may include one or more voxel sets of one or more VOIs 218, 220 in a 3D data set 203, wherein a part of each voxel set represents an abnormality. The segmentation module may subsequently classify and segment these voxels.

The deep neural networks of the detection module may be configured such that the detection module is capable of handling input data, a volume of voxels, of different sizes. Therefore, in an embodiment, the first 3D deep neural network may have a fully convolutional network architecture, that may include only valid padding layers and not striding or pooling layers. Additionally, due to the imaging settings of scanner systems that generate 3D data sets, many imaging modalities, such as (CB)CT data sets, often comprise highly anisotropic voxels, which means that not all three dimensions have the same resolution. The image resolution in the xy plane (a slice) may be much higher (more than ten times higher) than that the resolution in the z-direction. Thus, much more information is available within the xy plane than the z dimension. Direct application of 3D convolutional neural networks (CNNs) to a set of such highly anisotropic voxels may cause problems as it may be difficult to learn useful 3D features using 3×3×3 and 1×1×1 kernels as used by many 3D CNNs.

The problem of processing highly anisotropic 3D data sets by a 3D deep neural network, e.g. 3D CNNs, may be addressed by both 2D and 3D convolutional layers and using a reshaping operation to convert between them.

Figure 3A:
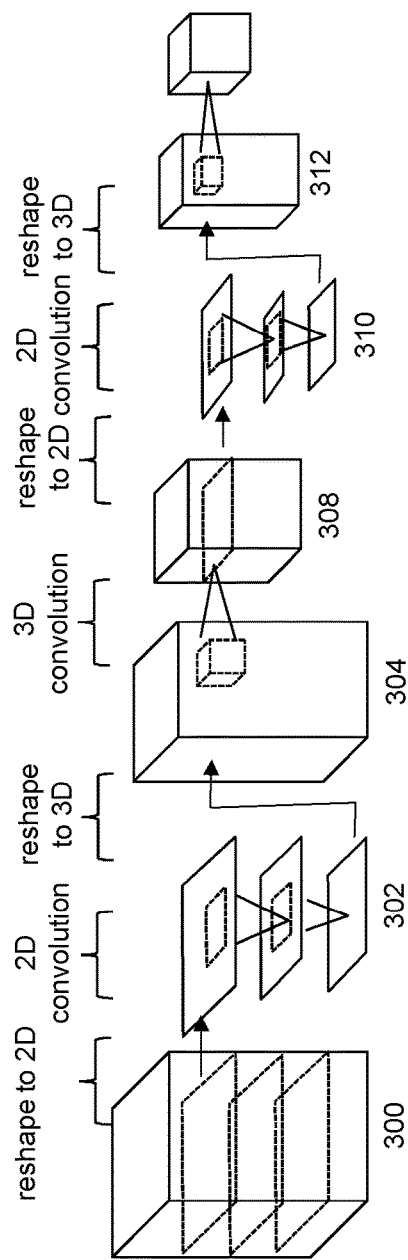
FIGS. 3A and 3B depicts a network architecture of a 3D deep neural network for a detection module according to an embodiment of the invention.
Figure 3B:
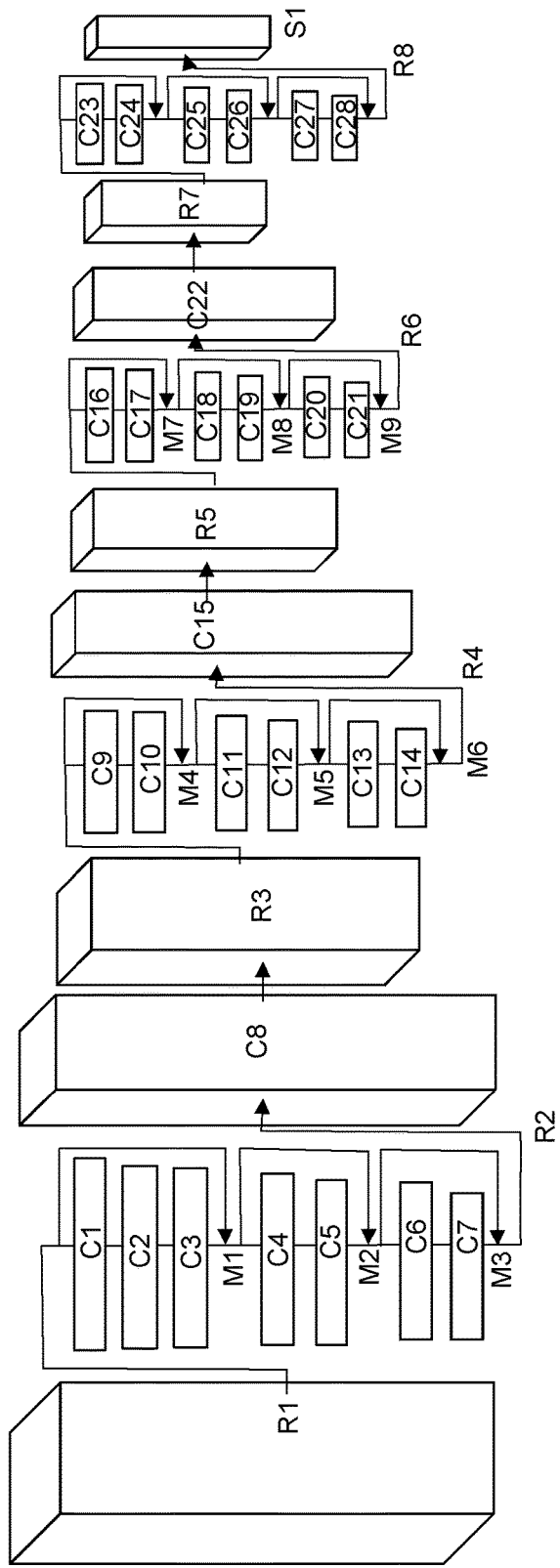

FIGS. 3A and 3B depicts a network architecture of a 3D deep neural network for a detection module according to an embodiment of the invention. In particular, this figure depicts an architecture of 3D deep neural network trained to process highly anisotropic 3D data sets, i.e. has resolution in the z-dimension than is substantially lower than the resolution in the x- and y-dimensions and derive a prediction of a position of a volume of interest VOI in the volume of the input data.

As shown in FIG. 3A, the deep neural network may include 3D CNNs and 2D CNNs wherein a well-known reshaping operation takes care for transitions between the 3D and 2D CNNs. For example, a first reshaping operation R1 may reshape slices of a first 3D (input) block 300 into a plurality of 2D slices, wherein each slice may be processed by a first 2D CNN 302 in which the dimensions of the slice are reduced. Thereafter, a second reshaping operation R2 may use the processed slices to build a second 3D block 304 of reduced xy dimensions. A first 3D convolutional operation may subsequently process the 3D block into a second 3D block 308 of reduced dimensions in three dimensions. Thereafter, the second 3D block may be processed by a second 2D CNN 310 in a similar way as described above. This process may be repeated several times. The inclusion of 2D convolutional layers may extend the network depth by operating only in the xy plane. This way the capabilities of the network to learn useful features of a highly anisotropic 3D data set is improved.

In an embodiment, the network architecture of the 2D CNN may include residual network blocks (ResNet) or blocks that provide functionality like ResNet blocks, e.g. ResNeXt blocks, where the input of a block is cropped and added to the output as is typical for a residual network. Addition is achieved using 'addition' layers. The residual blocks may improve the network depth (and therefor its capacity to determine useful features) without running into the so-called "vanishing gradients" problem.

In another embodiment, the 2D CNN may be configured as using dilated convolutions in order to gain a larger field of view per feature without requiring very large convolutional filters which are typically less efficient in terms of memory usage and computational resources. For example, the 2D CNNs may comprise blocks that may use dilated convolutions to process the data. For example, the first 2D CNN 302 may include convolutional layers of dilation 1, the second 2D CNN 310 may include convolutional layers of dilation 2, a third 2D CNN (not shown) may include convolutional layers of dilation 3, etc.

FIG. 3B depicts an overview of a neural network implementation according to an embodiment of the invention. The layers of the network and their dimensions are described hereunder in more detail with reference to table 1. As shown in FIG. 3B, the network may have an input 3D input layer 320 of predetermined dimensions (in this example 7×128× 128). As the input shape of 3D data sets that fed to the input layer are variable, the network may be implemented as a fully convolutional network (both the 3D and the 2D parts of the network). Hence, the dimensions of the input layer adapt to the dimensions of the 3D data set that is offered to the input of the network. The input layer may be followed by a reshape operation R1 so that slices of the 3D input layer can be processed by a first 2D CNN 322 including a plurality of 2D convolutional layers C1-C9 in a residual network configuration. For example, C1-C3 may form a first residual block, having two layers C1, C2 based on 3×3 convolutional kernels and a layer C3 based on a 1×1 convolutional kernel, wherein C1 has a dimension of 128×128, C2 a dimension of 126×126 and C3 a dimension of 124×124. Here, the first 2D CNN may comprise a first residual block wherein the input to layer C1 is added to the output of the C3 layer using an addition operation M1. In a similar way, the first 2D CNN may include a second and third residual block. The second residual block may include two layers C4, C5 based on a 3×3 and a 1×1 convolutional kernel respectively, wherein C4 has a dimension of 124×124 and C5 a dimension of 122×122 and wherein the input to layer C4 is added to the output of the C5 layer using an addition operation M2. Similarly, the third residual block may include two layers C6, C7 based on a 3×3 and a 1×1 convolutional kernel respectively, wherein C6 has a dimension of 122×122 and C5 a dimension of 120×120 and wherein the input to layer C6 is added to the output of the C7 layer using an addition operation M3. Thereafter, a reshape operation R2 may be executed which uses the processed slices of the input block into 7×120×120 3D block. A further 3D convolutional operation may reduce the 3D block into a 5×118×118 3D block. The process of reshaping the 3D block for a 2D CNN, processing the slices of the 3D block by the 2D CNN and reshaping the processed slices into a processed 3D block of reduced dimensions may be repeated several times. At the end the process, a last reshape operation R6 constructs in this example a 1×58×58 block which is subjected to a sigmoid operation. The result of the sigmoid operation is a rectangular block defining a candidate VOI in the volume of the input. The sigmoid delivers a per-voxel probability. Post-processing based on a threshold is used to locate maxima that represent locations of candidate VOIs. Table 1 describes the layers of an exemplary network architecture.

TABLE 1 overview of network layers of a deep neural network for determining candidate VOIs in a 3D data set.

| Layer | Input Shape | Type |
|---|---|---|
| Input | 7x128x128 | |
| R1 | 7x128x128 | Reshape to 2D |
| C1 | 128x128 | 3x3 conv |
| C2 | 126x126 | 3x3 conv |
| C3 | 124x124 | 1x1 conv |
| M1 | 2x124x124 | addition |
| C4 | 124x124 | 3x3 conv |
| C5 | 122x122 | 1x1 conv |
| M2 | 2x122x122 | addition |
| C6 | 122x122 | 3x3 conv |
| C7 | 120x120 | 1x1 conv |
| M3 | 2x120x120 | addition |
| R2 | 120x120 | Reshape to 3D |
| C8 | 7x120x120 | 3x3x3 convolution |
| R3 | 5x118x118 | Reshape to 2D |
| C9 | 118x118 | 3x3 conv dilation 2 |
| C10 | 114x114 | 1x1 conv |
| M4 | 2x114x114 | addition |
| C11 | 114x114 | 3x3 conv, dilation 2 |
| C12 | 110x110 | 1x1 conv |
| M5 | 2x110x110 | addition |
| C13 | 110x110 | 3x3 conv, dilation 2 |
| C14 | 106x106 | 1x1 conv |
| M6 | 2x106x106 | addition |
| R4 | 106x106 | Reshape to 3D |
| C15 | 5x106x106 | 3x3x3 conv |
| R5 | 104x104 | Reshape to 2D |
| C16 | 104x104 | 3x3 conv, dilation 3 |
| C17 | 98x98 | 1x1 conv |
| C18 | 98x98 | 3x3x3 conv, dilation 3 |
| C19 | 92x92 | 1x1 conv |
| M8 | 2x92x92 | addition |
| C20 | 92x92 | 3x3 conv, dilation 3 |
| C21 | 86x86 | 1x1 conv |
| M9 | 2x86x86 | addition |
| R6 | 86x86 | Reshape to 3D |

TABLE 1-continued overview of network layers of a deep neural network for determining candidate VOIs in a 3D data set.

| Layer | Input Shape | Type |
|---|---|---|
| C22 | 3x86x86 | 3x3x3 conv |
| R7 | 1x84x84 | Reshape to 2D |
| C23 | 84x84 | 3x3 conv, dilation 4 |
| C24 | 76x76 | 1x1 conv |
| M10 | 2x76x76 | addition |
| C25 | 76x76 | 3x3 conv, dilation 4 |
| C26 | 68x68 | 1x1 conv |
| M11 | 2x68x68 | addition |
| C27 | 68x68 | 3x3 conv, dilation 4 |
| C28 | 60x60 | 1x1 con |
| M12 | 2x60x60 | addition |
| C29 | 60x60 | 3x3 conv |
| R8 | 60x60 | Reshape to 3D |
| S1 | 1x58x58 | Sigmoid |

The example of table 1 describes an example wherein a 7×128×128 3D data set that is provided to the input layer of the network which is subsequently reduced to a 1×58×58 data set, however the network is configured to receive 3D data sets of variable size. For example, 3D data sets generated by current state of the art scanning system including around 150×500×500 voxels may be fed to the input of the neural network which generates an output label of 144×430×430 voxels, wherein each voxel defines a probability that the voxel is part of an abnormality. The input dataset may be padded so that the output label has the same shape as the input dataset. The voxel values may be evaluated based on a threshold value so that positions of voxels of a high enough probability may be used to identify one or more positions of a candidate VOI in the voxel space of the 3D data set that was provided to the input layer of the network.

Figure 4:
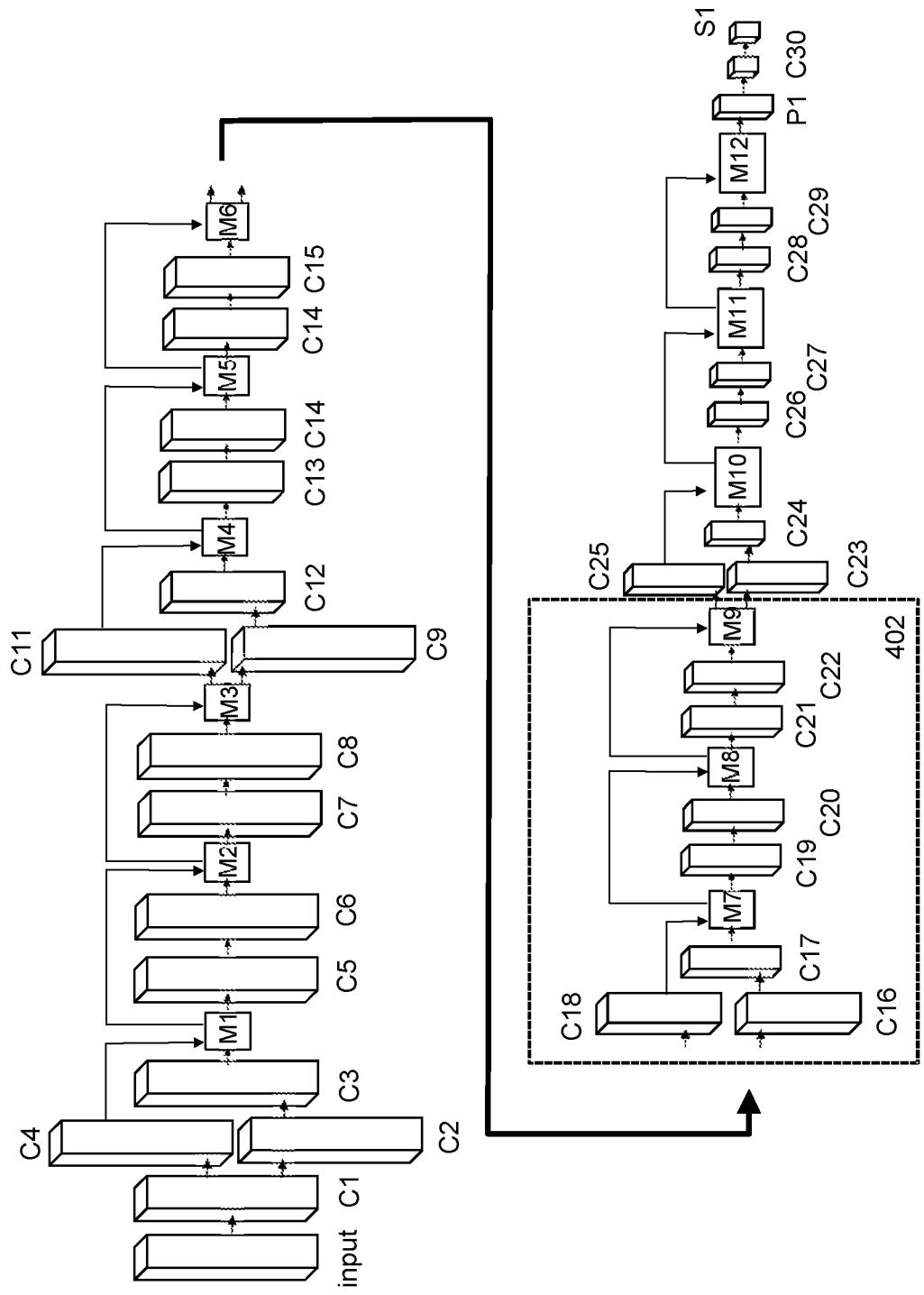
FIG. 4 depicts a schematic of a system for mapping VOI in 3D data sets according to an embodiment of the invention.

FIG. 4 depicts a network architecture of a 3D deep neural network for a detection module according to an embodiment of the invention. This network may be trained to receive (a set of) voxels of a candidate VOI in a 3D data set at its input. The position of the candidate VOI in the 3D data set may be determined based on the output of a deep neural network as described with reference to FIGS. 3A and 3B and determine an indicator whether or not the VOI comprises an abnormality. The input of the network is fixed so that techniques such as striding and padding can be used. Further, the 3D deep neural network includes a sequence of "super" residual network (resnet) blocks (e.g. block 402) including 3D CNN layers in a residual network type configuration in order to improve the network depth. In order to enable additions of the blocks of the same dimensions the resnet block includes a down sampling operation (in table 2 a stride of 2×2×2 may be regarded as a downsampling operation as the resolution is halved in the next layer). Finally, as one of the last layers a well-known global average pooling layer is used in order to efficiently obtain a single value without the need of additional convolutional layers. Table 2 describes the layers of an exemplary network architecture.

TABLE 2 overview of network layers of a deep neural network for determining if a candidate VOI comprises an abnormality.

| Layer | Input Shape | Type |
|---|---|---|
| Input | 13x72x72 | |
| C1 | 13x72x72 | 3x3x3 conv, same-padding |
| C2 | 13x72x72 | 3x3x3 conv, same-padding |
| C3 | 13x72x72 | 3x3x3 conv, same-padding |
| M1 | 2x13x72x72 | Addition of C3 and C4 |
| C4 | 13x72x72 | 1x1x1 conv |
| C5 | 13x72x72 | 3x3x3 conv, same-padding |
| C6 | 13x72x72 | 3x3x3 conv, same-padding |
| M2 | 2x13x72x72 | Addition of C6 and M1 |
| C7 | 13x72x72 | 3x3x3 conv, same-padding |
| C8 | 13x72x72 | 3x3x3 conv, same-padding |
| M3 | 2x13x72x72 | Addition of C8 and M2 |
| C9 | 13x72x72 | 3x3x3 conv, same-padding, stride 2x2x2 |
| C10 | 7x36x36 | 3x3x3 conv, same-padding |
| M4 | 2x7x36x36 | Addition of C10 and C11 |
| C11 | 13x72x72 | 1x1x1 conv, stride 2x2x2 |
| C12 | 7x36x36 | 3x3x3 con, same-padding |
| C13 | 7x36x36 | 3x3x3 conv, same-padding |
| M5 | 2x7x36x36 | Addition of C13 and M4 |
| C14 | 7x36x36 | 3x3x3 conv, same-padding |
| C15 | 7x36x36 | 3x3x3 con, same-padding |
| M6 | 2x7x36x36 | Addition of C15 and M5 |
| C16 | 7x36x36 | 3x3x3 conv, same-padding, stride 2x2x2 |
| C17 | 4x18x18 | 3x3x3 conv, same-padding |
| M7 | 2x4x18x18 | Addition of C17 and C18 |
| C18 | 7x36x36 | 1x1x1 convolution, stride 2x2x2 |
| C19 | 4x18x18 | 3x3x3 conv, same-padding |
| C20 | 4x18x18 | 3x3x3 conv, same-padding |
| M8 | 2x4x18x18 | Addition of C20 and M7 |
| C21 | 4x18x18 | 3x3x3 conv, same-padding |
| C22 | 4x18x18 | 3x3x3 conv, same-padding |
| M9 | 2x4x18x18 | Addition of C22 and M8 |
| C23 | 4x18x18 | 3x3x3 conv, same-padding, stride 2x2x2 |
| C24 | 2x9x9 | 3x3x3 conv, same-padding |
| M10 | 2x2x9x9 | Addition of C24 and M9 |
| C25 | 4x18x18 | 1x1x1 conv, same-padding, stride 2x2x2 |
| C26 | 2x9x9 | 3x3x3 conv, same-padding |
| C27 | 2x9x9 | 3x3x3 conv, same-padding |
| M11 | 2x2x9x9 | Addition of C27 and M10 |
| C28 | 2x9x9 | 3x3x3 conv, same-padding |
| C29 | 2x9x9 | 3x3x3 conv, same-padding |
| M12 | 2x2x9x9 | Addition of C29 and M11 |
| P1 | 2x9x9 | Global Average Pooling |
| C30 | 1x1x1 | 1x1x1 conv |
| S1 | 1x1x1 | Sigmoid |

Figure 5:
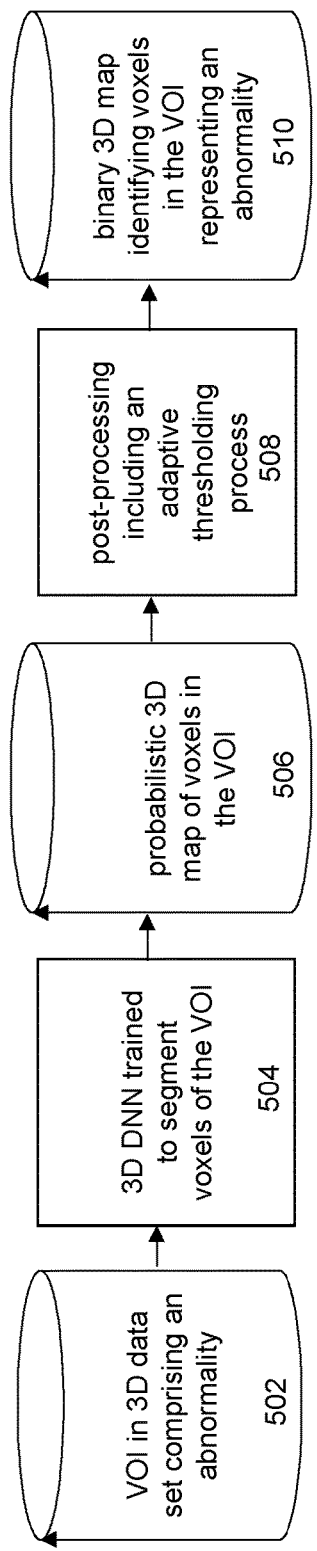
FIG. 5 depicts a segmentation module according to an embodiment of the invention.

FIG. 5 depicts a segmentation module according to an embodiment of the invention. As shown in this figure, the module may include a data storage 502 comprising one or more VOIs in a 3D data set as detected by the detection module described previously. The module may use a 3D deep neural network to segment an abnormality from the VOI. Hence, the 3D deep neural network may be trained to receive the voxels of the VOI at its input and determine whether each of the voxels of the VOI belongs to an abnormality or not. The output of the network may be a probabilistic map defining a 3D block of voxels positioned around the center of the VOI 506. Each voxel is associate with a probability value and a threshold value may be used to determine whether a voxel belongs to an abnormality. The sum of the probabilities of the voxels of the VOI provides an estimate of the nodule volume V. In order to create a binary segmentation based on the probabilistic output, a threshold may be selected such that the sum of the volume of voxels with a probability above the threshold is as close as possible to V. Since such threshold value is different for each segmentation, an adaptive thresholding scheme may be used for estimating a threshold value based on a search algorithm. This adaptive thresholding scheme may be executed as a post-processing step of the segmentation inference. This way, the segmentation module may determine a 3D binary voxel map for a voxel representation of a VOI, indicating which voxels of the voxel representation belong to an abnormality and which voxels belong to the context around the nodule. The 3D binary voxel map be positioned around the center of the VOI and its dimensions may be smaller than the dimensions of the voxel representation of the VOI.

Figure 6:
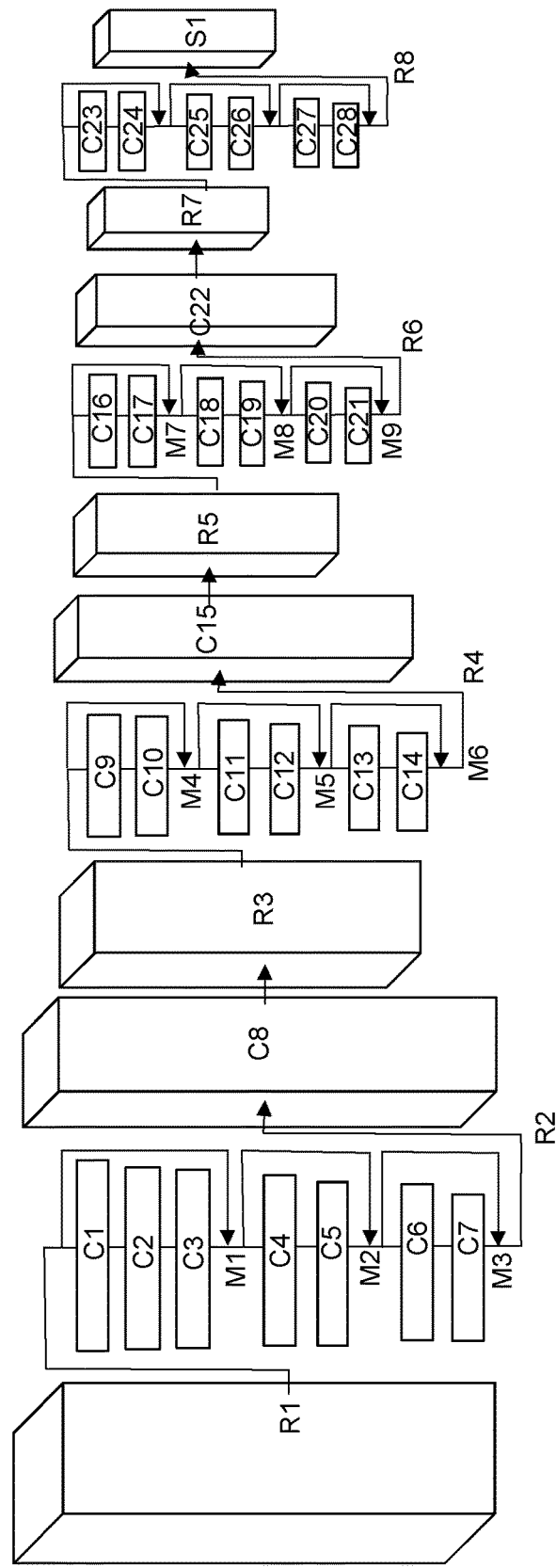
FIG. 6 depicts a network architecture of a 3D deep neural network for a segmentation module according to an embodiment of the invention.

FIG. 6 depicts a network architecture of a 3D deep neural network for a segmentation module according to an embodiment of the invention. The segmenting deep neural network should to be able to process sets of voxels that are highly anisotropic in terms of resolution. For that reason, a network architecture may be used that is similar to the network architecture of the network in the detection module that is trained for generating VOI candidates. Hence, the network may include both 3D CNNs and 2D CNNs, residual network blocks and/or dilated convolution operations to derive useful features from the voxels of the VOI that a presented to the input of the neural network. In this case however the dimensions of the input of the network are fixed and may be equal to the size of voxel representation of a VOI. Table 3 describes the layers of an exemplary network architecture.

TABLE 3 overview of network layers of a deep neural network for segmenting voxels of a VOI comprising an abnormality.

| Layer | Input Shape | Type |
|---|---|---|
| Input | 21x113x113 | |
| R1 | 113x113 | Reshape to 2D |
| C1 | 113x113 | 3x3 convolution |
| C2 | 111x111 | 3x3 convolution |
| C3 | 109x109 | 1x1 convolution |
| M1 | 2x109x109 | addition |
| C4 | 109x109 | 3x3 convolution |
| C5 | 107x107 | 1x1 convolution |
| M2 | 2x107x107 | addition |
| C6 | 107x107 | 3x3 convolution |
| C7 | 105x105 | 1x1 convolution |
| M3 | 2x105x105 | addition |
| R2 | 105x105 | Reshape to 3D |
| C8 | 21x105x105 | 5x3x3 convolutions [v |
| R3 | 17x103x103 | Reshape to 2D |
| C9 | 103x103 | 3x3 convolution, dilation 2 |
| C10 | 99x99 | 1x1 convolution |
| M4 | 2x99x99 | addition |
| C11 | 99x99 | 3x3 convolution, dilation 2 |
| C12 | 95x95 | 1x1 convolution |
| M5 | 2x95x95 | addition |
| C13 | 95x95 | 3x3 convolution, dilation 2 |
| C14 | 91x91 | 1x1 convolution |
| M6 | 2x91x91 | addition |
| R4 | 17x91x91 | Reshape to 3D |
| S1 | 9x43x43 | Sigmoid [probability] |
| C15 | 17x91x91 | 5x3x3 convolution |
| R5 | 89x89 | Reshape to 2D |
| C16 | 89x89 | 3x3 convolutions, dilation 3 |
| C17 | 83x83 | 1x1 convolution |
| M7 | 2x83x83 | addition |
| C18 | 83x83 | 3x3 convolutions, dilation 3 |
| C19 | 77x77 | 1x1 convolution |
| M8 | 2x77x77 | addition |
| C20 | 77x77 | 3x3 convolutions, dilation 3 |
| C21 | 71x71 | 1x1 convolution |
| M9 | 2x71x71 | addition |
| R6 | 71x71 | Reshape to 3D |
| C22 | 13x71x71 | 5x3x3 convolution |

TABLE 3-continued overview of network layers of a deep neural network for segmenting voxels of a VOI comprising an abnormality.

| Layer | Input Shape | Type |
|---|---|---|
| R7 | 71x71 | Reshape to 2D |
| C23 | 69x69 | 3x3 convolution, dilation 4 |
| C24 | 61x61 | 1x1 convolution |
| M10 | 2x61x61 | addition |
| C25 | 61x61 | 3x3 convolution, dilation 4 |
| C26 | 53x53 | 1x1 convolution |
| M11 | 2x53x53 | addition |
| C27 | 53x53 | 3x3 convolution dilation 4 |
| C28 | 45x45 | 1x1 convolution |
| M12 | 2x45x45 | addition |
| C29 | 45x45 | 1x1 convolution |
| R8 | 45x45 | Reshape to 3D |

FIG. 7 depicts a registration module according to an embodiment of the invention. As described with reference to FIG. 1, if at least one first VOI 704 comprising voxels associated with an abnormality is detected in a current 3D data set, the system may look for a relevant prior 3D data set of the same patient and determine if at least one second VOI 702 is present in the prior 3D data set that represents an abnormality. If at least one VOI is detected in both the current and prior 3D data set, the detected VOIs may be evaluated by a registration module 704 in order to determine if the VOIs are associated with the same abnormality. To that end, the registration module comprises at least two inputs, e.g. a first input for receiving a voxel set of a VOI in the current 3D data set and a voxel set of a VOI in the prior 3D data set. Both sets may be evaluated based on a non-rigid transform that is applied to the whole voxel space of the two 3D data sets. The non-rigid transform will register the voxel space of both 3D data sets, including the VOIs in both 3D data sets. Based on the registered VOIs a mapping M function may be determined. Based on a VOI comprising an abnormality a detected by the detection module, the mapping function M will return a VOI comprising a corresponding abnormality b in the prior 3D data set, i.e.: b=M(a). Well-known non-rigid transforms such as e.g. a B-spline transform or the like may be used to register the 3D data sets. This way, a first VOI in the current 3D data set can be linked to a second VOI in the prior 3D data set.

One disadvantage of the registration module depicted in FIG. 7 is that the processing of the entire 3D data sets by the non-rigid transform may be computationally intensive. Therefore, in an embodiment, a registration process may be used that is based on a 3D deep neural network. A schematic of such registration module is depicted in FIGS. 8A and 8B. As shown in FIG. 8A, the module comprises a storage for storing the positions of one or more VOIs in the prior 3D data set 802 and the positions of one or more VOIs of the current 3D data set 804 and a 3D deep neural network 806 that is trained to determine a similarity score between two voxel representations, a voxel representation of a VOI of the current 3D data set and a voxel representation of a VOI of the prior 3D data set. Then, based on the stored VOIs, the module may determine all combinations of sets of voxel representations of a VOI of the prior 3D data set and a VOI of the current 3D data set and determine for each of these sets a similarly score by providing the voxel representation of each set to the input of the 3D deep neural network. This way, the registration module may determine similarity scores 808 for all possible combinates of VOIs from the prior and current 3D data set, wherein a similarity score defines a probability that a voxel presentation of a VOI in the current 3D data set and a voxel representation of a VOI in the prior 3D data set represent the same abnormality. The similarity scores may be ordered in a similarity matrix. Further, as shown in FIG. 8B, in a second phase, a processor 812 of the registration module may be configured to execute a linear optimization algorithm based on the similarity matrix S 810 to determine an optimal mapping function M 814 between VOIs of the current 3D data set and VOIs of the prior 3D data set. Thus, the determination of the mapping function may look as follows:

Input: list of abnormality locations $L_0$ and $L_1$ for 3D data sets at timestamps $T_0$ and $T_1$ respectively.
For each abnormality $A_0$ in $L_0$
  For each abnormality $A_1$ in $L_1$
    Calculate the similarity score $S(A_0,A_1)$
Output: Similarity matrix S with dimension $|L_0| \times |L_1|$.
Given the similarity matrix S, calculate the optimum mapping M between $L_0$ and $L_1$ that maximizes the mapping likelihood by formulating the determination of the optimum mapping M as a linear programming problem and applying the Simplex algorithm.

An example of a similarity matrix associated with 5 abnormalities in $L_0$ and 4 in $L_1$ may look as follows:

[ 1.   0.47  0.   0.   0.  ]
[ 0.34 1.   0.   0.   0.  ]
[ 0.   0.   1.   0.   0.  ]
[ 0.   0.   0.   0.2  0.04]

The mapping function M will return a VOI comprising a corresponding abnormality b in the prior 3D data set, i.e.: b=M(a). The registration module of FIGS. 8A and 8B thus determines a mapping function based on a trained 3D deep neural network that is configured to compare a VOI of a prior 3D data set with a VOI of a current 3D data set. This way, the registration module does not need to determine a registration of the whole 3D data sets. Instead, only patches (small sub-parts) of the prior and current 3D data sets are registered, thereby substantially reducing the computational load of the registration module, when compared to a registration module based on a conventional non-rigid transform registration algorithm.

Figure 9:
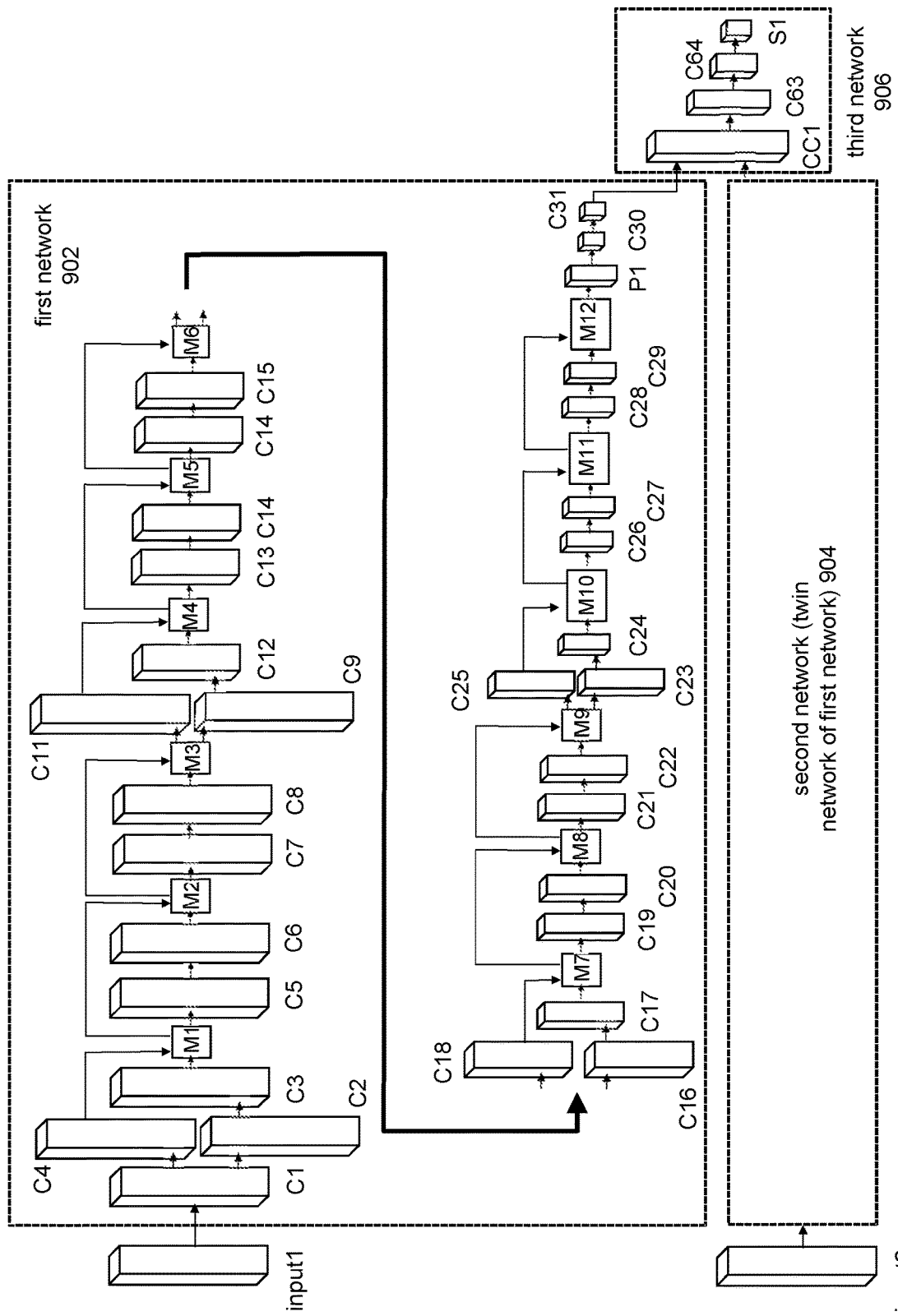
FIG. 9 depicts a network architecture of a 3D deep neural network for a registration module according to an embodiment of the invention.

FIG. 9 depicts a network architecture of a 3D deep neural network for a registration module according to an embodiment of the invention. The deep neural network may be configured as a so-called Siamese twin network, including a first deep neural network branch 902 trained to process a first voxel representation of a VOI and a second neural network branch 904 trained to process a second voxel representation of a VOI, wherein first and second neural network are identical (same weights). The outputs of the first and second neural network are processed by a third neural network 906 that compares the outputs of both networks and determines a similarity measure. Table 4 provides describes the layers of an exemplary network architecture.

TABLE 4 overview of network layers of a deep neural network for determining registration of an abnormality in two 3D data sets.

| Layer | Input Shape | Type |
| --- | --- | --- |
| Input | 13x72x72 | |
| C1 | 13x72x72 | 3x3x3 convolution, same-padding |
| C2 | 13x72x72 | 3x3x3 convolution, same-padding |
| C3 | 13x72x72 | 3x3x3 convolution, same-padding |
| M1 | 2x13x72x72 | Addition of C3 and C4 |
| C4 | 13x72x72 | 1x1x1 convolution |
| C5 | 13x72x72 | 3x3x3 convolution, same-padding |
| C6 | 13x72x72 | 3x3x3 convolution, same-padding |
| M2 | 2x13x72x72 | Addition of C6 and M1 |
| C7 | 13x72x72 | 3x3x3 convolution, same-padding |
| C8 | 13x72x72 | 3x3x3 convolution, same-padding |
| M3 | 2x13x72x72 | Addition of C8 and M2 |
| C9 | 13x72x72 | 3x3x3 convolution, same-padding, stride 2x2x2 |
| C10 | 7x36x36 | 3x3x3 convolution, same-padding |
| M4 | 2x7x36x36 | Addition of C10 and C11 |
| C11 | 13x72x72 | 1x1x1 convolution, stride 2x2x2 |
| C12 | 7x36x36 | 3x3x3 convolution, same-padding |
| C13 | 7x36x36 | 3x3x3 convolution, same-padding |
| M5 | 2x7x36x36 | Addition of C13 and M4 |
| C14 | 7x36x36 | 3x3x3 convolution, same-padding |
| C15 | 7x36x36 | 3x3x3 convolution, same-padding |
| M6 | 2x7x36x36 | Addition of C15 and M5 |
| C16 | 7x36x36 | 3x3x3 convolution, same-padding, stride 2x2x2 |
| C17 | 4x18x18 | 3x3x3 convolution, same-padding |
| M7 | 2x4x18x18 | Addition of C17 andC18 |
| C18 | 7x36x36 | 1x1x1 convolution, stride 2x2x2 |
| C19 | 4x18x18 | 3x3x3 convolution, same-padding |
| C20 | 4x18x18 | 3x3x3 convolution, same-padding |
| M8 | 2x4x18x18 | Addition of C20 and M7 |
| C21 | 4x18x18 | 3x3x3 convolution, same-padding |
| C22 | 4x18x18 | 3x3x3 convolution, same-padding |
| M9 | 2x4x18x18 | Addition of C22 and M8 |
| C23 | 4x18x18 | 3x3x3 convolution, same-padding, stride 2x2x2 |
| C24 | 2x9x9 | 3x3x3 convolution, same-padding |
| M10 | 2x2x9x9 | Addition of C24 and M9 |
| C25 | 4x18x18 | 1x1x1 convolution, same-padding, stride 2x2x2 |
| C26 | 2x9x9 | 3x3x3 convolution, same-padding |
| C27 | 2x9x9 | 3x3x3 convolution, same-padding |
| M11 | 2x2x9x9 | Addition of C27 and M10 |
| C28 | 2x9x9 | 3x3x3 convolution, same-padding |
| C29 | 2x9x9 | 3x3x3 convolution, same-padding |
| M12 | 2x2x9x9 | Addition of C29 and M11 |
| C30 | 2x9x9 | 1x3x3 convolution |
| C31 | 2x7x7 | 1x3x3 convolution |

TABLE 4-continued overview of network layers of a deep neural network for determining registration of an abnormality in two 3D data sets.

| Layer | Input Shape | Type |
| --- | --- | --- |
| Input | 13x72x72 | |
| CC1 | 2x2x7x7 | Concatenation with siamese twin branch |
| C63 | 2x5x5 | 2x5x5 convolution |
| C64 | 1x1x1 | 1x1x1 convolution |
| S1 | 1x1x1 | Sigmoid |

As shown in this table, the first and second deep neural network branch may include a sequence of "super" residual network (resnet) blocks including 3D convolutions in a residual network type configuration in order to improve the network depth (similar to the network architecture described with reference to FIG. 4).

Figure 10:
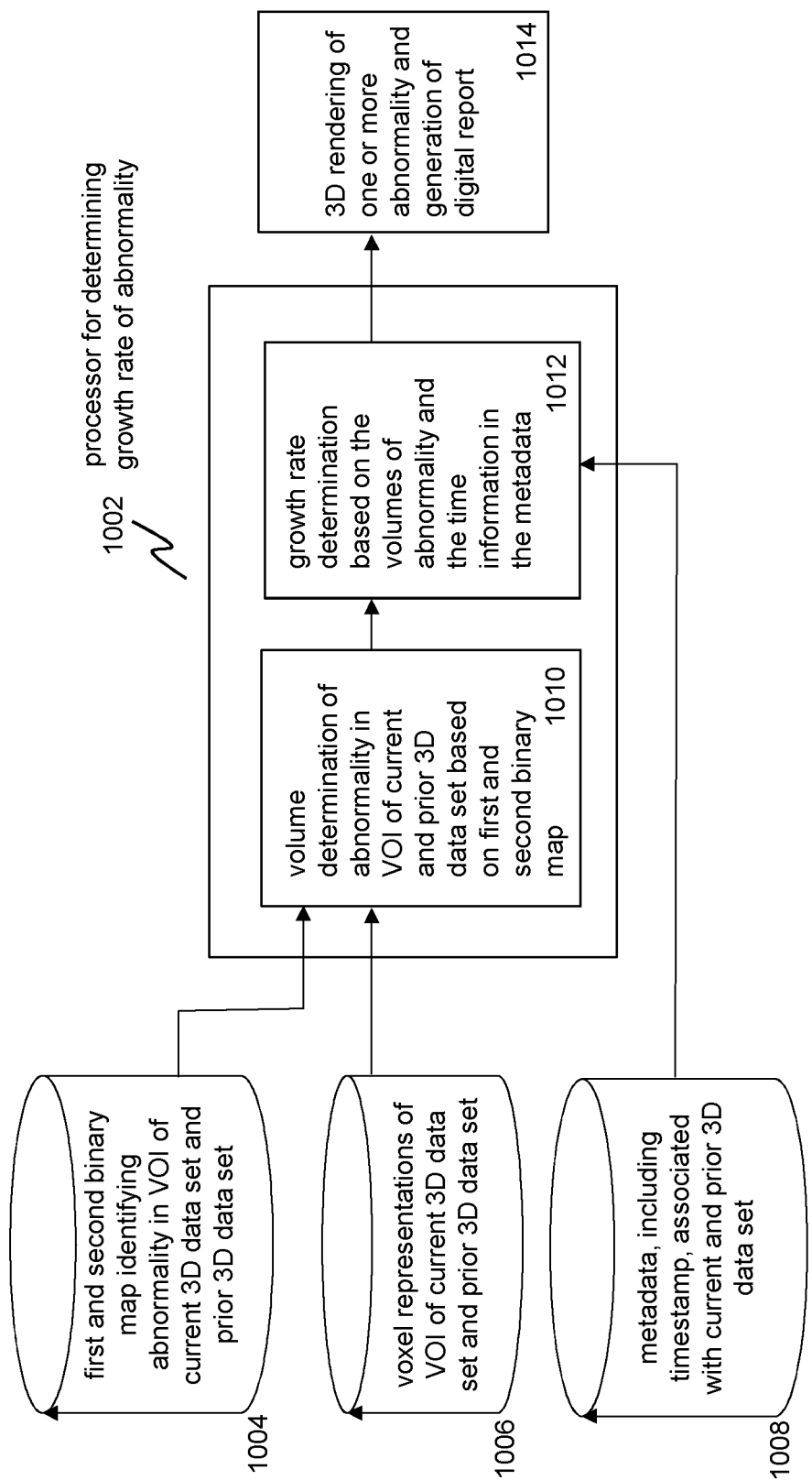
FIG. 10 depicts module for determining a growth rate according to an embodiment of the invention.

FIG. 10 depicts growth rate module according to an embodiment of the invention. As described with reference to FIG. 1, the growth rate module is configured to determine a volume for an abnormality detected in a current 3D data set and a corresponding abnormality in a prior 3D data set. The volume may be determined based the binary map that is determined by the segmentation map. As already described with reference to FIG. 5, the 3D binary map identifies voxels in a VOI that quality as voxels belonging to an abnormality, wherein the sum of the volumes of the voxels identified by the binary map provides an estimate of the volume of the abnormality. Thus, based on the 3D binary map and voxel representation of a VOI of the current 3D data set and a voxel representation of a corresponding VOI of the prior 3D data set, volumes $V_0$ and $V_1$ 1010 of the abnormality in the prior 3D data set and the current 3D data set respectively can be determined. Here, a volume of an abnormality may be determined by summing volumes of voxels that are identified by a binary map as belonging to the abnormality. Based on these volumes and, optionally, additional metadata a growth rate metric 1012 may be determined. For example, a growth percentage (GP) may be calculated. Additionally, based on metadata associated with the prior and current 3D data sets, in particular the time instances $T_0$ and $T_1$ at which the 3D data sets were generated; can be used together with the volumes in order to determine the Volume Doubling Time (VDT).

The outputs of the modules of the system may be used to generate 3D renders of an abnormality in the current and prior 3D data set. For example, based on segmented voxels of the VOI a 3D surface mesh of the abnormality may be determined. Further, a digital report including the 3D renders and the growth rate metric(s) associated with the 3D renders may be generated.

Figure 11A:
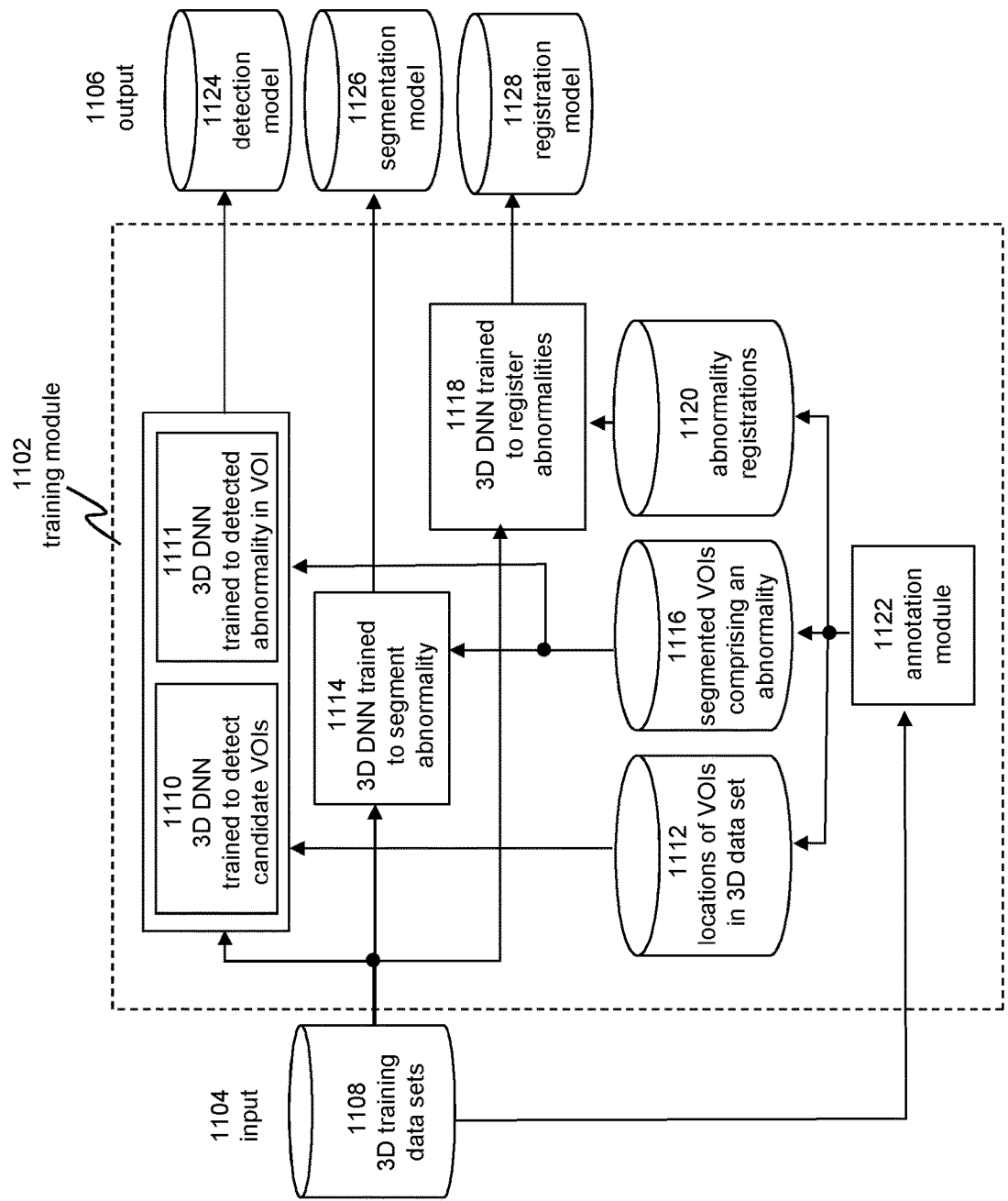
FIG. 11 depicts a training module for training deep neural networks of detecting, segmenting and registration of an abnormality in a 3D data set according to an embodiment of the invention.
Figure 11B:
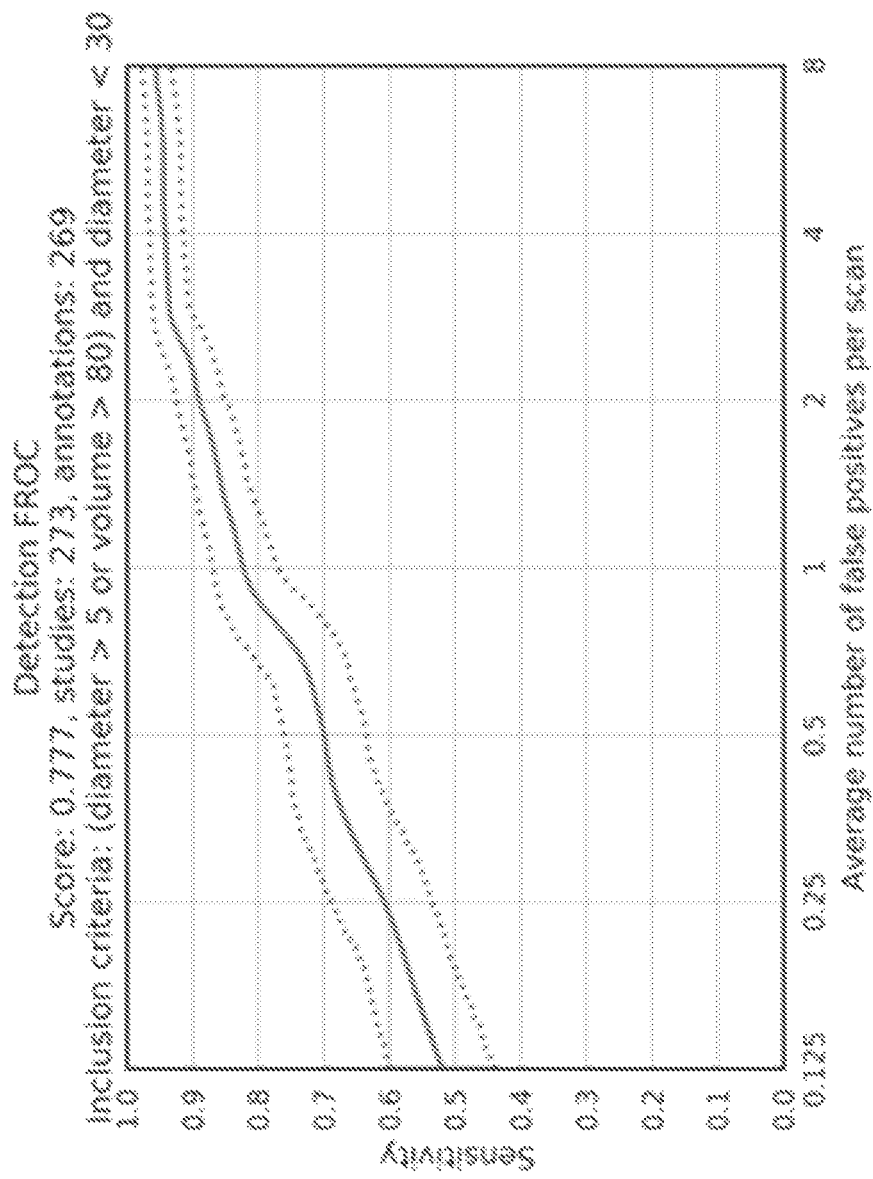

FIG. 11A depicts a training module for training the 3D deep neural networks of the modules in the system. FIG. 11B depicts a FROG curve of a trained 3D DNN system of a detection module of the system. During the training phase of the 3D DNNs, 3D training data sets 1108, i.e. a large dataset of suitable 3D data sets, typically 3D CT scans, together with manually and/or computer-created labels, is used to iteratively update a model (represented by the network parameters, e.g. the weights, of the neural network) a large number of times, A well-known stochastic gradient descent optimization method may be used to slowly learn the correct values of the network parameters of each of the 3D DNNs by reducing the error between the output of the neural network and the correct labels. When the error rate stops decreasing the training phase of a network is completed.

This process is applied for the each 3D DNN of the system, including at least: 3D deep neural networks for detecting abnormalities 1110, a 3D DNN for segmenting an abnormality in a VOI 1114 and a 3D DNN for registering abnormalities of a prior and a current 3D data set 1118.

The training phase may include a preprocessing step that may involve one or more of the following steps:

1. determining a large set of 3D data sets, e.g. studies of different patients including 3D CT scans of the relevant body part as training set, wherein a study typically may comprise of several 3D data sets, each taken with a different acquisition plane (e.g. sagittal or coronal) and reconstruction kernels;
2. selection one or more 3D data sets based on radiological expertise that have the highest relevance for the detection of les ions, preferably the selected 3D data sets having a MOM format (or another suitable standard) or being transformed into a DICOM format (or another suitable standard);
3. conversion of the one or more selected 3D data sets to a format that is suitable for subsequent processing by the modules in the system, in particular, as part of the conversion, the resolution of the one or more selected 3D data sets may be standardized in 3 dimensions.

Next annotations 1122 are generated for the selected 3D data sets. The annotations may be determined qualified readers (typically experienced radiologists) to indicate abnormalities in slices of each of the 3D data sets. A computer-aided image annotation system may be used to annotate the slices. The annotation system may be configured to navigate through slices of a 3D data set, select and display a slice and apply image processing to a slice (including image reconstruction in multiple planes and maximum intensity projection (MIP)). The annotation system may allow a user to graphically determine locations of abnormalities in slices and determine an outline of each abnormalities in slices of 3D training data sets. For segmentation, the annotation system may include a touch-sensitive pencil or stylus for drawing the outlines of an abnormality in slices of a 3D data set. Further, for the registration model, the reader may indicate which abnormality in a slice of a prior 3D data set belongs to an abnormality in a slice of a current prior data set. The annotations, i.e. the determined abnormality locations 1112, the abnormality segmentations 1116 and the abnormality registrations 1120 may be stored and used by the training module to train the 3D deep neural networks of the system.

The detection module includes two 3D deep neural networks (DNN): a first 3D DNN for generation of VOI candidates, which receives a 3D data set (or a large part thereof) as input and outputs a target label representing a 3D coordinate of one or more potential abnormality locations; and, a second 3D DNN for false positive reduction, which receives voxels associated with a VOI in a 3D data set, wherein the position of the VOI is provided by the first (candidate generation) 3DNN and outputs a target label representing a score that corresponds to the probability that voxels of the VOI represent an abnormality. Both the first and second 3D DNNs are trained on a large set of manually annotated locations 1112, typically at least several thousand.

The 3D DNN of the segmentation module is trained to receive voxels associated with a VOI in a 3D input data set. The output of the network is a 3D probabilistic mask indicating a probability that a voxel at the input data set belongs to an abnormality. This network is trained on a large set (typically around a thousand) of manually segmented abnormalities 1116.

The 3D DNN of the registration module is configured to receive a first and second voxel set of a first and second VOI (as determined by the detection module) at its input and is trained to output a score between 0 and 1 indicating the probability that the two voxel sets include an abnormality that relates to the same abnormality. This network is trained on a large set of manually annotated abnormality registrations 1120, where a second VOI is created by applying 3D non-linear transformations on the original first VOI.

For example, training of the 3D DNN of the segmentation module based on the scheme of FIG. 11A may include the steps of:

1. extraction of a ROI and a position of the ROI in multiple series of slices of a training data set. Here, a series of slices may form a 3D data set and the ROI of the different slices may form voxels of a VOI at a particular location in the 3D data set, wherein the voxels of the VOI include voxels representing an abnormality;

2. determination of a target label associated with each VOI wherein the target label represents probabilistic 3D map of the same or similar dimensions as the block of voxels of the VOI that are offered to the input of the 3D DNN, Elements of the 3D map correspond to voxels of the VOI wherein each element is associated with a probability regarding the chance that 8 corresponding voxel belongs to an abnormality;

3. providing voxels of a VOI of the training set to the input of a 3D DNN and using a loss function for determining an error based on the output of the 3D DNN and the correct output label associated with the VOI, 4. applying a backpropagation to improve the network parameters and repeating this process until the error between the predicted output label and the correct output label converges.

Each of the 3D DNN may be trained in a similar way based appropriate input data and target labels (as indicated by FIG. 11A). The performance of the trained 3D DNNs were evaluated based on 3D data sets that were both processed by a trained 3D DNN and medical experts (typically radiologists).

The performance of the 3D DNN for segmenting VOIs is provided in Table 1. The table depicts a comparison between the segmentation of nodules performed by a medical expert (i.e. "manual" segmentation by processing slices of a VOI using standard software tools) and segmentation performed by a 3D DNN that is trained to perform segmentation of a VOI (as described within this application). The results are derived on the basis of 428 nodules which represents a set of nodules which in terms of composition and size distribution can be considered to be a proper representation of clinical practice and thus suitable for the purpose of a clinical evaluation performance. The table includes both segmentation results as well as volume and diameter determination based on the segmentation results:

TABLE 1 performance of the segmentation network and volume and diameter determination of a nodule based a segmented VOI.
ALL NODULES (n = 428)

| | Segmentation Average Dice + CI (Perfect agreement × 1.0) | Volume Mean discrepancy + CI (Theorectical optimum: 1.17) | Diameter Mean discrepancy + CI (Theorectical optimum: 1.07) |
| --- | --- | --- | --- |
| Inter-radiologist score | 0.83(0.39, 0.96) | 1.39 (1.01, 3.19) | 1.15 (1.00, 1.58) |
| Veye vs radiologists score (95% of detected nodules of which the device was able to create a segmentation) | 0.86 (0.51, 0.95) | 1.38 (1.01, 3.38) | 1.15 (1.00, 1.69) |

As shown in table 1, only a small discrepancy is present between volumes determined by the medical specialists and volumes determined by the system based on a 3D DNN that is trained to segment a VOI. The results indicate that the system is able to determine a volume of a nodule with an accuracy that is at least comparable to the accuracy of a medical specialist. Hence, the performance of the segmenting module is equivalent to that of a radiologist which is considered acceptable for clinical practice. Moreover, improvements of the system may be achieved by improving the training of the neural network.

The performance of the 3D DNNs of the detection is given in the form of a FROC curve as depicted by FIG. 11B. The curve is based on the analysis of 269 nodules (diameter larger than 5 mm and volume larger 80 $mm^3$) than were evaluated by both medical experts and a trained 3D CNN pair, i.e. a 3D CNN trained to determine VOI candidates in a 3D data set and a 3D CNN trained to evaluate the candidate VOIs. The figure illustrates the trade-off between sensitivity and false positive rate. The higher the FROG curve, the better. Each point on the FROG curve corresponds to a threshold value (at the left edge the threshold is 1 and at the right edge the threshold is zero. The detection module outperforms a medical expert when the detection threshold is set to ≥1 false positive per study on average. As shown by the FROG curve, the sensitivity is about 94% at an average number of 4 false positives per scan. The performance of the detection module is considered acceptable for clinical practice.

The performance of the 3D DNN for registering VOIs is provided in Table 2. The table depicts the results of a comparison between registration of 26 pairs of nodules. If the matching 3D DNN identified a positive pair it was scored as a true positive pair (TP pair). A false positive pair (FP pair) was scored when the matching 3D DNN matched nodules that are not a pair according to the reference standard. As shown in the table, no false positive pairs were predicted by the neural network:

Results Matching

| | | Prediction | | |
|---|---|---|---|---|
| Reference | | TP pair | FP pair | T1 nodules correctly not matched (TN) |
| Standard | TP pair (26) | 26 | 0 | 16* |

Only TP nodules - based on majority consensus - are included in the reference standard
*This number shows a certain level of complexity of the validation dataset. There are 16 positve nodules that could have been matched incorrectly but were not.

The performance shows that the registration module for matching nodules of a current study with a prior study is considered acceptable for clinical practice. Hence, the performances of the trained neural networks show that the system is capable of detecting, segmenting and registering abnormalities in 3D data sets with an accuracy that is at least similar to the evaluation of 3D data sets by a medical expert. As described with reference to FIG. 1, the system is capable of receiving a current 3D data set of a patient and—if the system determines that the current 3D data set includes one or more abnormalities—automatically determine a prior 3D data set of the same patient on the basis of the metadata of the current 3D data set. To that end, the interface processor of the system and the PACS system may communicate with each other based on a suitable protocol. Preferably the protocol may be based on the DICOM standard, which is an international standard to transmit, store, retrieve, process, and display medical imaging information.

Figure 12:
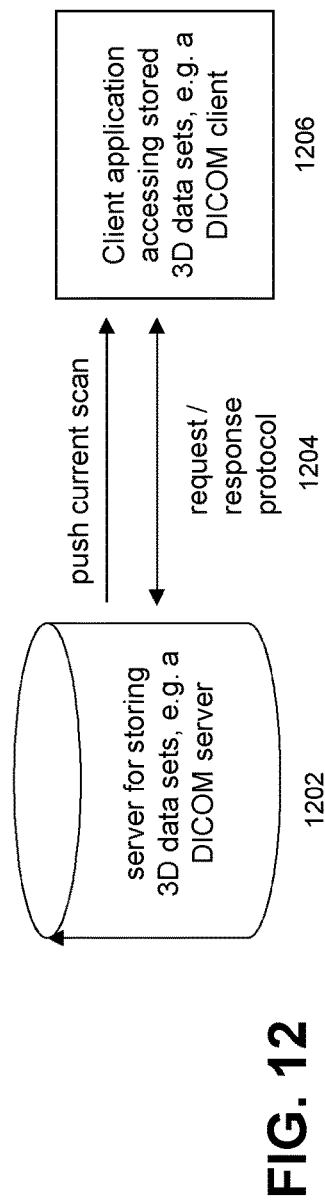
FIG. 12 depicts an example of a client server system for storing and retrieval of 3D data sets.

FIG. 12 depicts an example of a client server system including a server 1202 for storing 3D data sets in a standardized data format, e.g. the DICOM data format. The 3D data sets can be accessed by client devices 1206 which are configured to communicate which the server based on a standardized protocol 1204. Such as the DICOM protocol. In a typical configuration, the interface processor of the system of FIG. 1 may include a client device and the server may be part of the PACS system. The client server system is configured to retrieve a prior study, a prior 3D data set, that can be used a comparison to assess the growth rate of an abnormality.

Figure 13:
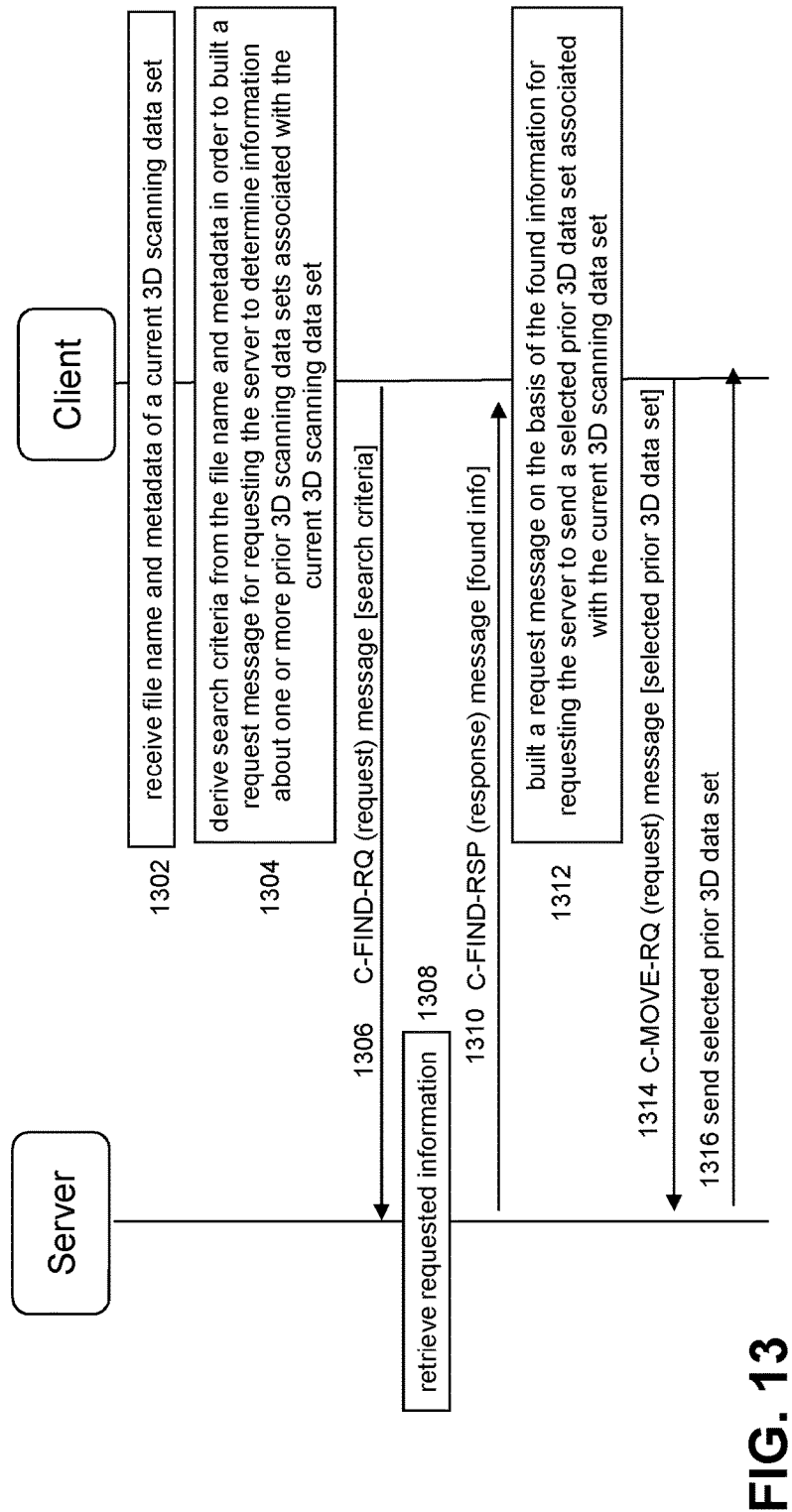
FIG. 13 depicts a sequence of protocol messages for retrieval of 3D data sets.

A typical sequence of protocol messages for retrieval of 3D data sets is shown in FIG. 13. The example is illustrated based on the DICOM standard, however the process may be implemented on any suitable database query protocol. In a first step 1302, a client device may receive a file name associated with a current 3D data set. The client device may use metadata associated with the file name to determine a request message (step 1304) for requesting the server to determine information about one or more prior 3D scanning data sets associated with the current 3D scanning data set. Thereafter, the client device may send a request message C-FIND-RQ to the server (step 1306). The request message may include one or more Q/R queries sent to the server. An example of such query may look as follows:
QueryRetrieve level: STUDY
Query model: P (patient)
Query parameters:
  PatientID=<patient_id>
  StudyDate=<range> (e.g. '20080101-20180505')
  StudyInstanceUID="# empty (provided by PACS in response message)
  AccessionNumber=" # empty (provided by PACS in response message)
The server may determine one or more prior studies of the patient (step 1308) and send the information in a response message C-FIND-RSP back to the client device (step 1310).

The client device may filter the information in order to reduce the list to those studies that relate to a CT modality and contain information about the chest part of the body. Preferably, the list includes prior studies that are at least two months earlier than the current study. If there are multiple prior studies, the most recent study may be selected. The client device may be built a further request message (step 1312) on the basis of the information provided by the server. The further request message C-MOVE-RQ may be sent to the server (step 1314) and in response the server sends the selected prior 3D data set (step 1316) associated with the current 3D scanning data set.

Figure 14:
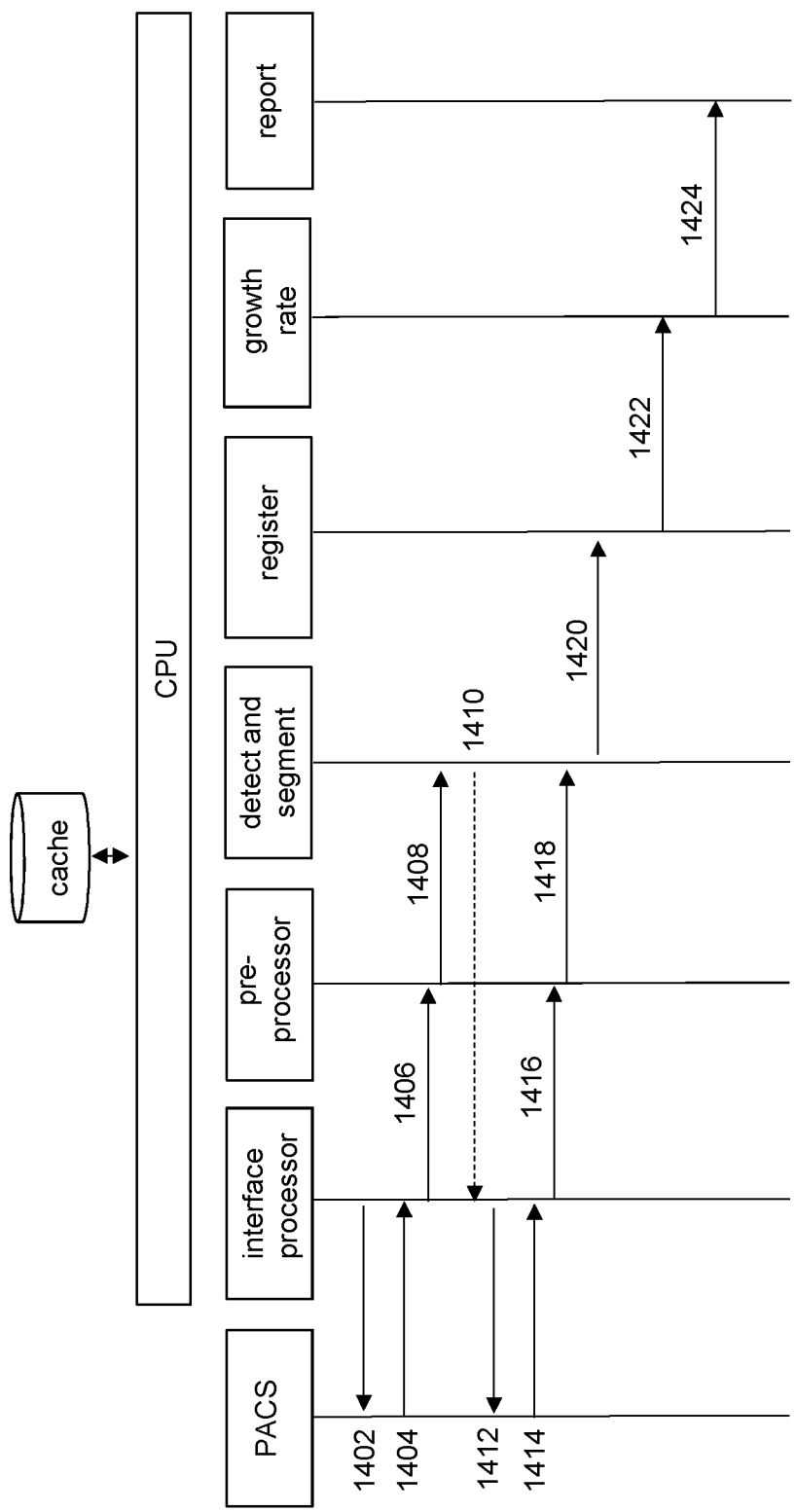
FIG. 14 depicts a flow diagram of a process for automatic determining a growth rate of an abnormality in 3D data sets according to an embodiment of the invention.

FIG. 14 depicts a flow diagram of a process for automatic determining a growth rate of an abnormality in 3D data sets according to an embodiment of the invention. In particular, the flow diagram illustrates the automatic retrieval of a prior 3D data set from the PACS system as described with reference to FIGS. 12 and 13. As shown in this figure, the process is managed by a central processor CPU of the system which controls and executes the different modules of the system. The process may start with the CPU instructing the interface process to retrieve a current study, e.g. a current 3D data set, which needs to be clinically asserted with respect to the presence of abnormalities, including an estimate of the growth rate of an abnormality. The interface processor may send (at least) a request message to the PACS system (step 1402) for requesting a current 3D data set and in response to the request the PACS system may send (at least) a response message (step 1404) including current 3D data set and metadata associated with the current 3D data set to the interface processor. Dependent on the protocol that is implemented for communication between the interface processor and the PACS system, the communication between the interface processor and the PACS system may include multiple request and response messages, as e.g. illustrated in FIG. 13 regarding the DICOM protocol. The selected 3D data set may be normalized by a pre-processor (step 1406) and subsequently processed by the detection module and the segmentation module (step 1408). Here, the detection module detects one or more VOIs in the 3D data set wherein each VOI contains voxels associated with an abnormality and the segmentation module segments the voxels of each detected VOI and produces a probabilistic 3D map of the voxels of the VOI. The probabilistic 3D map may be transformed into a binary 3D map based on e.g. an adaptive thresholding process. The binary 3D map identifies voxels in the current 3D data set that are part of an abnormality, wherein the sum of the voxel volumes of voxels that are identified by the binary 3D map represents the volume of the abnormality.

If the CPU concludes that one or more VOIs are detected and segmented, the CPU instructs the interface processor to retrieve a prior study, e.g. a prior 3D data set, of the same patient. To that end, the interface processor constructs a request message on the basis of the metadata of the current 3D data set and sends the request message to the PACS (step 1412), which uses the metadata in the request message to look for a suitable prior 3D data set. If the PACS system finds a suitable prior 3D data set, it will send the prior data set and metadata associated with the prior data set in a response message to the interface processor (step 1414). Also in this case, based on the protocol that is used, the message exchange between the interface processor and the PACS may include multiple messages. Then, the prior 3D data set may be processed in a similar way as the current 3D data set, including normalization (step 1416) and detection and segmentation (step 1418) resulting in one or more VOIs that include an abnormality and for each VOI a binary 3D map that identifies the voxels in the prior 3D data that belong to an abnormality. Hence, if the CPU concludes that the prior 3D data set contains abnormalities, then it sends the VOIs of the current and prior 3D data set to the registration module for registering the abnormalities of the current and prior 3D data set (step 1420). The registration module may produce a mapping M between VOIs in the current and prior 3D data set, wherein the mapping M links a VOI in the current 3D data set that is associated with an abnormality to a VOI in the prior 3D data set that is associated with the same abnormality. Thereafter, a growth rate module may receive the mapping M indicating one or more pairs of VOIs, one in the current 3D data set and one in the prior 3D data set, that relate to the same abnormality, metadata associated with the current and prior 3D data set (in particular information at what time instance the data were generated) and binary 3D maps of each of the one or more pairs of VOIs, wherein each binary 3D map provides a measure of the volume of an abnormality. Based on this information, the growth rate module may determine a growth rate metric for each abnormality (step 1422). The results of the process may be communicated to an expert in a human-readable format. To that end, an electronic report may be generated that comprises information determined by the modules, e.g. the growth rate metric, 3D segmented VOIs of abnormalities in current and prior 3D data sets, etc. As the entire process is fully automated it is important that the information enables a medical specialist to verify that the calculation of the growth rate metrics was correctly performed. The report therefore also includes a visualization of the segmentation model a 2D or 3D rendering of the current and prior 3D data set. An example of an electronic report is depicted in FIG. 16, illustrating metrics 1602 (volume and diameter) of a detected current and prior nodule that were determined by the system; slices 1604 of a current and prior 3D data set in which the (shape and position of) nodules are visually identified by contours; and, 3D renders 1606 of the detected current and prior nodule.

Figure 15:
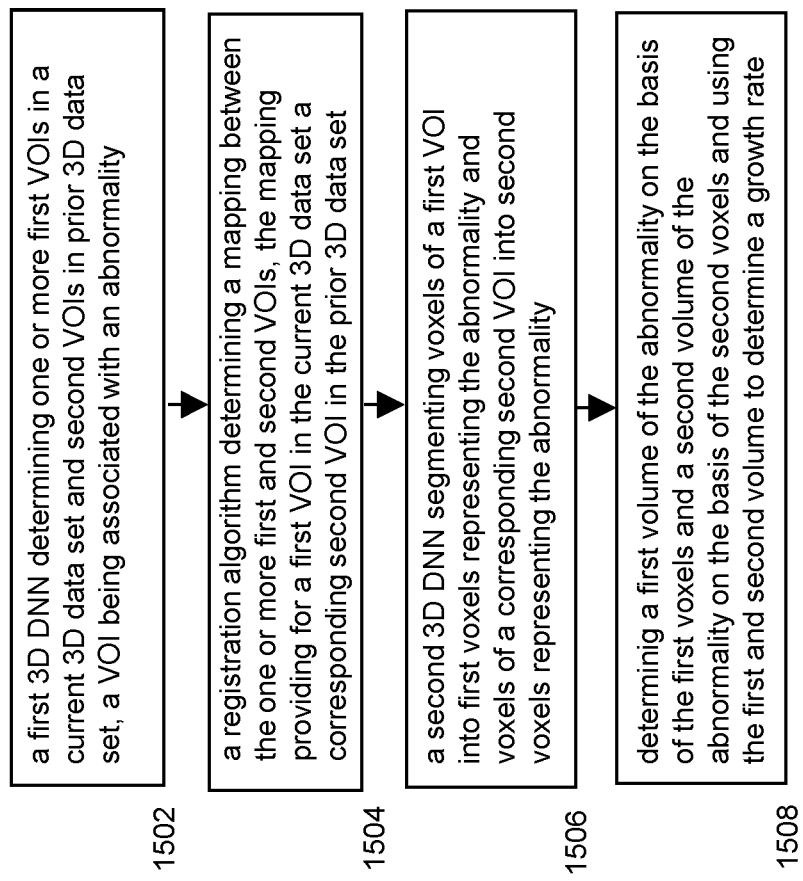
FIG. 15 depicts a flow diagram of a process for automatic determining a growth rate of an abnormality in 3D data sets according to another embodiment of the invention.

FIG. 15 depicts a general flow diagram of the automatic determining a growth rate of an abnormality in 3D data sets according to an embodiment of the invention. As shown in this figure, the invention includes the steps of: a first 3D DNN determining one or more first VOIs in a current 3D data set and second VOIs in prior 3D data set, a VOI being associated with an abnormality (step 1502); a registration algorithm, preferably a registration algorithm including a third 3D DNN, determining a mapping between the one or more first and second VOIs, the mapping providing for a first VOI in the current 3D data set a corresponding second VOI in the prior 3D data set (step 1504); a second 3D DNN segmenting voxels of a first VOI into first voxels representing the abnormality and voxels of a corresponding second VOI into second voxels representing the abnormality (step 1506); and, determining a first volume of the abnormality on the basis of the first voxels and a second volume of the abnormality on the basis of the second voxels and using the first and second volume to determine a growth rate (step 1508).

Figure 16:
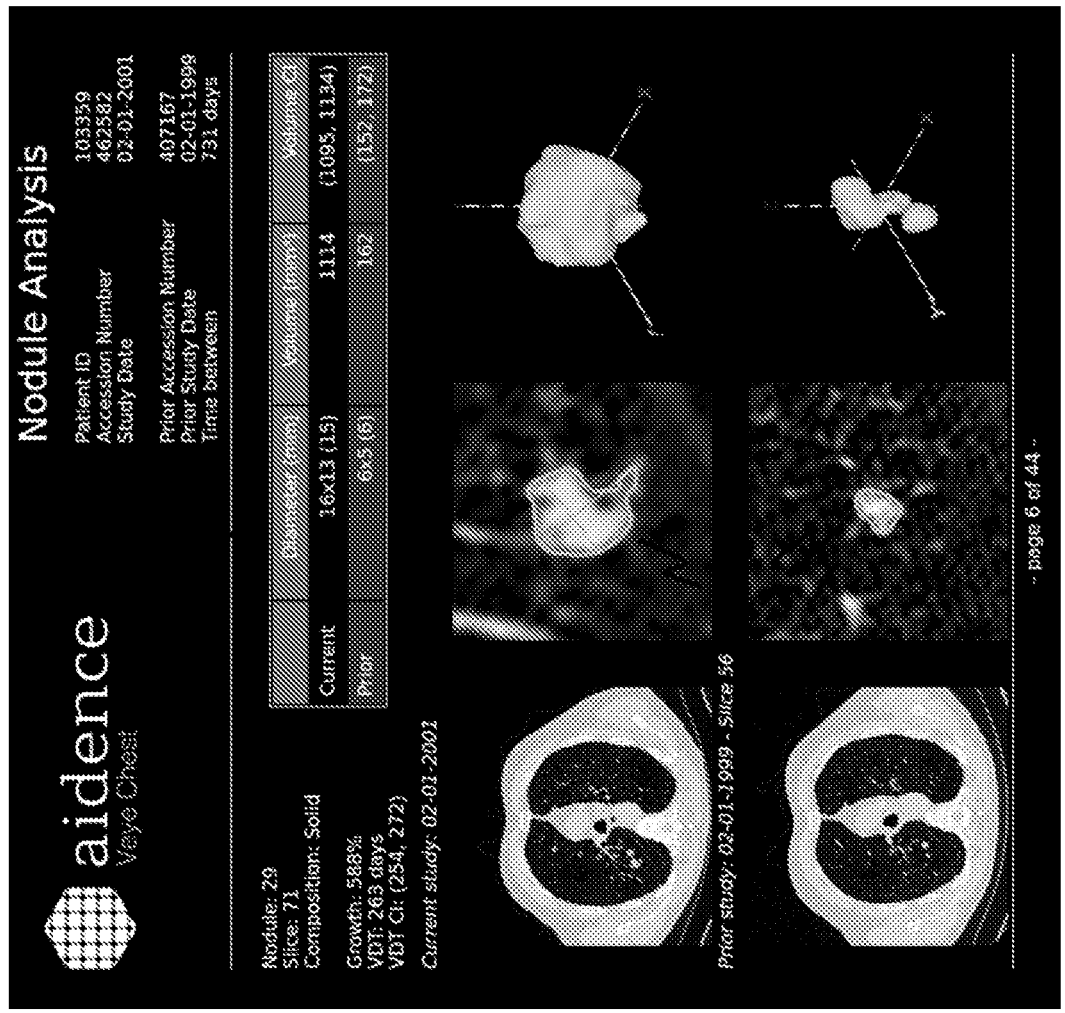
FIG. 16 depicts an example of an electronic report generated by a system for automatic determining a growth rate of an abnormality in 3D data sets according to an embodiment of the invention.
Figure 17:
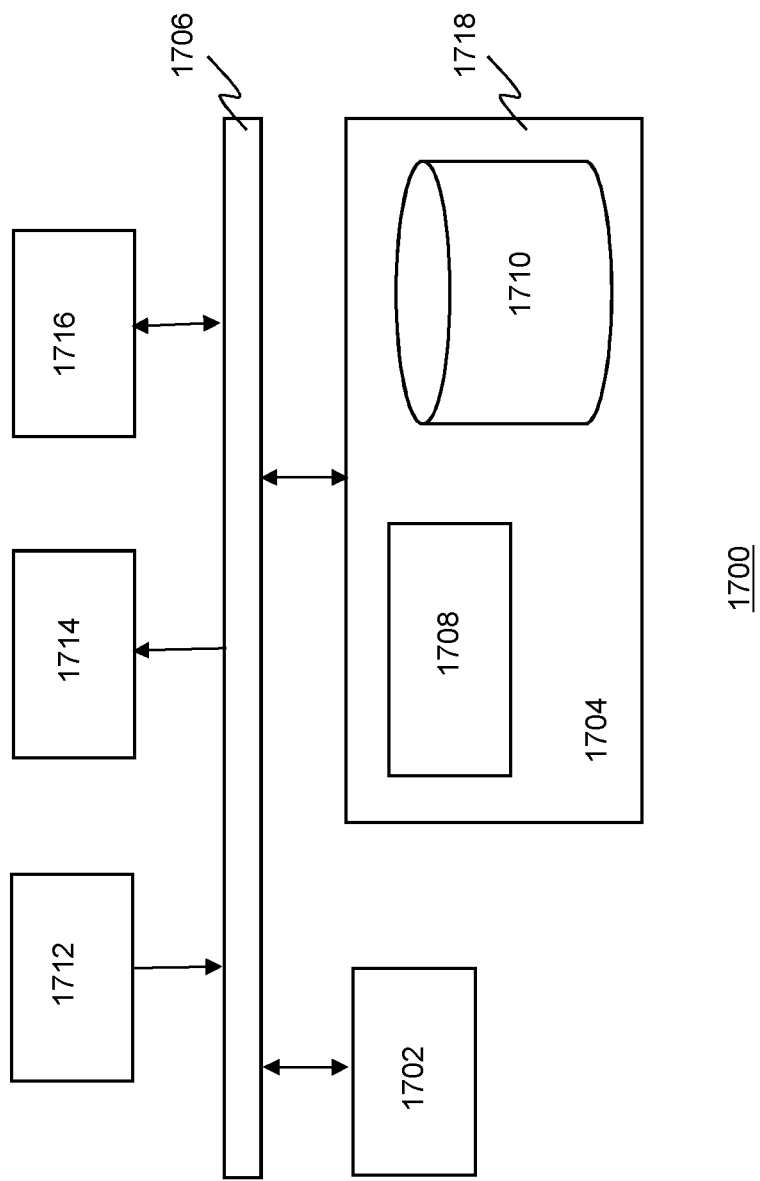
FIG. 17 is a block diagram illustrating an exemplary data processing system that may be used for executing methods and software products described in this application.

FIG. 16 is a block diagram illustrating an exemplary data processing system that may be used in as described in this disclosure. Data processing system 1600 may include at least one processor 1602 coupled to memory elements 1604 through a system bus 1606. As such, the data processing system may store program code within memory elements 1604. Further, processor 1602 may execute the program code accessed from memory elements 1604 via system bus 1606. In one aspect, data processing system may be implemented as a computer that is suitable for storing and/or executing program code. It should be appreciated, however, that data processing system 1600 may be implemented in the form of any system including a processor and memory that is capable of performing the functions described within this specification.

Memory elements 1604 may include one or more physical memory devices such as, for example, local memory 1608 and one or more bulk storage devices 1610. Local memory may refer to random access memory or other non-persistent memory device(s) generally used during actual execution of the program code. A bulk storage device may be implemented as a hard drive or other persistent data storage device. The processing system 1600 may also include one or more cache memories (not shown) that provide temporary storage of at least some program code in order to reduce the number of times program code must be retrieved from bulk storage device 1610 during execution.

Input/output (I/O) devices depicted as input device 1612 and output device 1614 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 1616 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 1600.

As pictured in FIG. 16, memory elements 1604 may store an application 1618. It should be appreciated that data processing system 1600 may further execute an operating system (not shown) that can facilitate execution of the application. Application, being implemented in the form of executable program code, can be executed by data processing system 1600, e.g., by processor 1602. Responsive to executing application, data processing system may be configured to perform one or more operations to be described herein in further detail.

In one aspect, for example, data processing system 1600 may represent a client data processing system. In that case, application 1618 may represent a client application that, when executed, configures data processing system 1600 to perform the various functions described herein with reference to a "client". Examples of a client can include, but are not limited to, a personal computer, a portable computer, a mobile phone, or the like.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A method for automated determination of a growth rate of a first abnormality from one or more abnormalities in a body part of a patient, the method comprising:
   a processor providing a current 3D data set associated with a first time instance to a first 3D deep neural network (DNN) system, the current 3D data set defining a first voxel representation of the body part of the patient, the first 3D DNN system being trained (i) to receive the current 3D data set, (ii) to determine whether the current 3D data set comprises the one or more abnormalities and (iii), if the current 3D data set comprises the one or more abnormalities, to output one or more first volumes of interest (VOIs) in the current 3D data set, each of the one or more first VOIs being associated with a respective abnormality from the one or more abnormalities;
   the processor receiving the one or more first VOIs in the current 3D data set from the first 3D DNN system;
   the processor providing a prior 3D data set associated with a second time instance to the first 3D DNN system, the prior 3D data set defining a second voxel representation of the body part of the patient;
   the processor receiving one or more second VOIs in the prior 3D data set from the first 3D DNN system;
   the processor using a registration algorithm to register the one or more first VOIs with the one or more second VOIs, the registration algorithm generating a mapping, the mapping determining, for a first VOI in the current 3D data set, a corresponding second VOI in the prior 3D data set, the first VOI and the corresponding second VOI being associated with a same abnormality from the one or more abnormalities;
   the processor providing voxels of the first VOI a second 3D DNN system, the second 3D DNN system being trained (i) to receive voxels of the first VOI and (ii) to output a first 3D map defining probabilities for the voxels of the first VOI, a probability associated with a voxel defining a chance that the voxel is part of the one or more abnormalities;
   the processor receiving the first 3D map from the second 3D DNN system;
   the processor providing voxels of the corresponding second VOI to the second 3D DNN system;
   the processor receiving a second 3D map from the second 3D DNN system;
   the processor using (i) the first 3D map to identify first voxels in the current 3D data set representing the first abnormality and (ii) the second 3D map to identify second voxels in the prior data set representing the first abnormality; and;
   the processor determining a first volume of the first abnormality based on the first voxels and a second volume of the first abnormality based on the second voxels and using the first volume and second volume to determine the growth rate of the first abnormality from the one or more abnormalities in the body part of the patient.

2. The method according to claim 1, further comprising:
   after receiving the one or more first VOIs, the processor using metadata associated with the current 3D data set to construct a request message and to send the request message to a database, the request message instructing the database to send the prior 3D data set to the processor.

3. The method according to claim 1, wherein the first 3D DNN system includes:
   at least a first 3D deep convolutional neural network (CNN), the first 3D deep CNN being trained to receive the current 3D data set and to output locations within the current 3D data set of one or more candidate VOIs, each candidate VOI defining a location in the current 3D data set at which the abnormality may be present; and
   at least a second 3D deep CNN, the second 3D deep CNN being trained to receive a candidate VOI from the one or more candidate VOIs from the first 3D deep CNN and to determine a probability that voxels of the candidate VOI represent the abnormality.

4. The method according to claim 1, wherein the registration algorithm includes a non-rigid transform to register voxels of the current 3D data set with voxels of the prior 3D data set.

5. The method according to claim 1, wherein the registration algorithm comprises a third 3D DNN system trained to receive the first VOI of the current 3D data set and the second VOI of the prior 3D data set and to output a similarity score, the similarly score defining a measure regarding similarity between voxels of the first VOI and voxels of the second VOI.

6. The method according to claim 5, wherein the registration algorithm generating the mapping includes:
   determining a similarity matrix comprising probability scores associated with combinations of a first VOI selected from the one or more first VOIs in the current 3D data set and a second VOI selected from the one or more second VOIs in the prior 3D data set; and
   using a linear optimization algorithm based on the similarity matrix to determine an optimal mapping between the one or more first VOIs of the current 3D data set and the one or more second VOIs of the prior 3D data set.

7. The method according to claim 5, wherein the first 3D DNN system or the third 3D DNN system comprises a 3D residual convolutional neural network.

8. The method of claim 5, wherein the third 3D DNN system is configured as a 3D deep Siamese neural network, the 3D deep Siamese neural network including a first 3D deep neural network part for receiving and processing the first VOI and a second 3D deep neural network part, wherein the first and second 3D deep neural network parts share same weights.

9. The method according to claim 1, wherein:
   a first threshold is applied to the probabilities in first 3D map to form a first 3D binary map identifying the first voxels in the current 3D data set; and
   a second threshold is applied to the probabilities in the second 3D map to form a second 3D binary map to identify the second voxels in the prior 3D data set.

10. The method of claim 9, wherein the first threshold is selected such that the sum of voxel volumes identified by the first 3D binary map represents the volume of the abnormality in the current 3D data set and the second threshold is selected such that the sum of voxel volumes identified by the second 3D binary map represents the volume of the abnormality in the prior 3D data set.

11. The method according to claim 1, wherein the method further comprises a step of:
generating a digital report associated with the current 3D data set and the prior 3D data set, the digital report including a 3D graphical representation of the abnormality in the current 3D data set and a 3D graphical representation of the abnormality in the prior 3D data set and the growth rate of the abnormality.

12. The method according to claim 1, wherein the first 3D DNN system and/or the second 3D DNN system comprises one or more blocks of convolutional layers, each block including a 3D CNN and a 2D CNN, wherein a reshaping operation reshapes slices of the 3D CNN into a plurality of 2D slices, wherein each 2D slice is processed by the 2D CNN.

13. The method according to claim 1, wherein the storage and the retrieval of the current and prior 3D data sets are based on a DICOM standard.

14. Computer program product stored on a non-transitory computer-readable medium, the computer program product comprising software code portions configured for, when run in the memory of a computer, executing the method according to claim 1.

15. The method of claim 1, wherein the current 3D data set and the prior 3D data set are CT scans of the body part of the patent.

16. A method of training a plurality of 3D deep neural networks (DNNs), the method comprising the steps of:
receiving a training set for training a plurality of 3D DNNs, the training set including 3D data sets, wherein each of the 3D data sets either comprise zero or one or more abnormalities and one or more volume of interests (VOIs) for at least part of the 3D data sets, each VOI being associated with an abnormality;
receiving, for each VOI, a pixel representation of the VOI, location information indicating at which location the VOI is located in a 3D data set, and a probabilistic 3D map defining probabilities for voxels of the VOI, a probability associated with a voxel defining a chance that the voxel is part of an abnormality;
training a first 3D DNN using voxel representations of the 3D data sets as input and the location information as a target;
training a second 3D DNN using voxel representations of the VOIs as input and the probabilistic 3D map associated with the voxel representations of the VOIs as the target; and
training a third 3D DNN using voxel representations of the VOIs and non-linear image transformations of the voxel representations of the VOIs as input and similarity scores as the target, a similarity score defining a similarity between a voxel representation of a VOI and a non-linear image transformation of the voxel representation.

17. The method of claim 16, wherein the current 3D data set and the prior 3D data set are CT scans, of the body part of the patent.

18. A computer system for automated determination of a growth rate of a first abnormality from one or more abnormalities in a body part of a patient, the computer system comprising:
a non-transitory computer-readable storage medium having computer-readable program code embodied therewith, the program code including at least one trained 3D deep neural network, and
at least one processor coupled to the computer-readable storage medium, wherein, responsive to executing the computer-readable program code, the at least one processor is configured to perform executable operations comprising:
providing a current 3D data set associated with a first time instance to a first 3D deep neural network (DNN) system, the current 3D data set defining a first voxel representation of the body part of the patient, the first 3D DNN system being trained (i) to receive the current 3D data set, (ii) to determine whether the current 3D data set comprises the one or more abnormalities and (iii), if the current 3D data set comprises the one or more abnormalities, to output one or more first volumes of interest (VOIs) in the current 3D data set, the one or more VOIs being associated with the a respective abnormality from the one or more abnormalities;
receiving the one or more first VOIs in the current 3D data set from the first 3D DNN system;
providing a prior 3D data set associated with a second time instance to the first 3D DNN system, the prior 3D data set defining a second voxel representation of the body part of the patient;
receiving one or more second VOIs in the prior 3D data set from the first 3D DNN system;
using a registration algorithm to register the one or more first VOIs with the one or more second VOIs, the registration algorithm generating a mapping, the mapping determining, for a first VOI in the current 3D data set, a corresponding second VOI in the prior 3D data set, the first VOI and the corresponding second VOI being associated with a same abnormality from the one or more abnormalities;
providing voxels of the first VOI to a second 3D DNN system, the second 3D DNN system being trained to receive voxels of the first VOI and to output a first 3D map defining probabilities for voxels of the first VOI, a probability associated with a voxel defining a chance that the voxel is part of the one or more abnormalities;
receiving the first 3D map from the second 3D DNN system;
providing voxels of the corresponding second VOI to the second 3D DNN system;
receiving a second 3D map from the second 3D DNN system;
using the first 3D map to identify first voxels in the current 3D data set representing the first abnormality;
using the second 3D map to identify second voxels in the prior data set representing the first abnormality; and
determining a first volume of the first abnormality based on the first voxels and a second volume of the first abnormality based on the second voxels and using the first volume and second volume to determine the growth rate of the first abnormality from the one or more abnormalities in the body part of the patient.

19. The computer system according to claim 18, wherein the first 3D DNN system includes:
- at least a first 3D deep convolutional neural network (CNN), the first 3D deep CNN being trained to receive the current 3D data set and to output locations within the current 3D data set of one or more one candidate VOIs, each candidate VOI defining a location in the current 3D data set at which an abnormality may be present; and
- at least a second 3D deep CNN, the second 3D deep CNN being trained to receive a candidate VOI from the one or more candidate VOIs from the first 3D deep CNN and to determine a probability that voxels of the candidate VOI represent the abnormality.

20. The computer system of claim 19, wherein the third 3D DNN system is configured as a 3D deep Siamese neural network, the 3D deep Siamese neural network including a first 3D deep neural network part for receiving and processing the first VOI and a second 3D deep neural network part, wherein the first and second 3D deep neural network parts share same weights.

21. The computer system according to claim 18, wherein the registration algorithm comprises a third 3D DNN system trained to receive the first VOI of the current 3D data set and the second VOI of the prior 3D data set at its input and to determine a similarity score at its output, the similarly score defining a measure regarding similarity between voxels of the first VOI and voxels of the second VOI.

\* \* \* \* \*